United States Patent [19]

Hiratsuka et al.

[11] Patent Number: 5,129,938

[45] Date of Patent: Jul. 14, 1992

[54] PYRIMIDINE DERIVATIVES

[75] Inventors: Mitsunori Hiratsuka, Toyonaka; Naonori Hirata, Sanda; Kazuo Saitoh; Hideyuki Shibata, both of Toyonaka, all of Japan

[73] Assignee: Sumitomo Chemical Company, Limited, Osaka, Japan

[21] Appl. No.: 733,870

[22] Filed: Jul. 22, 1991

[30] Foreign Application Priority Data

Jul. 26, 1990 [JP] Japan ................... 2-199763
Apr. 25, 1991 [JP] Japan ................... 3-125495

[51] Int. Cl.$^5$ ............... A01N 43/54; C07D 239/60
[52] U.S. Cl. ............................. 71/92; 544/300; 544/301; 544/302; 544/303; 544/310; 544/311; 544/312; 544/313; 544/314; 544/316; 544/318
[58] Field of Search ............. 544/300, 301–303, 544/310–314, 316, 318; 71/92

[56] References Cited

U.S. PATENT DOCUMENTS

| | | | |
|---|---|---|---|
| 4,248,619 | 2/1981 | Serban et al. | 71/92 |
| 4,871,387 | 10/1989 | Sasse et al. | 544/314 |
| 4,900,352 | 2/1990 | Wada et al. | 544/314 |
| 4,946,495 | 8/1990 | Wada et al. | 71/92 |
| 4,968,340 | 11/1990 | Kaku et al. | 71/92 |
| 4,973,354 | 11/1990 | Hatanaka et al. | 71/92 |
| 4,985,066 | 1/1991 | Wada et al. | 71/92 |

FOREIGN PATENT DOCUMENTS

| | | |
|---|---|---|
| A39549 | 3/1990 | Australia . |
| 0223406 | 5/1987 | European Pat. Off. . |
| 0249707 | 12/1987 | European Pat. Off. . |
| 0249708 | 12/1987 | European Pat. Off. . |
| 0287072 | 10/1988 | European Pat. Off. . |
| 0287079 | 10/1988 | European Pat. Off. . |
| 0335409 | 4/1989 | European Pat. Off. . |
| 0314623 | 5/1989 | European Pat. Off. . |
| 0315889 | 5/1989 | European Pat. Off. . |
| 0321846 | 6/1989 | European Pat. Off. . |
| 0336494 | 10/1989 | European Pat. Off. . |
| 0346789 | 12/1989 | European Pat. Off. . |
| 0360163 | 3/1990 | European Pat. Off. . |
| 0372329 | 6/1990 | European Pat. Off. . |
| 0374839 | 6/1990 | European Pat. Off. . |
| 0402751 | 6/1990 | European Pat. Off. . |
| 3927382 | 8/1989 | Fed. Rep. of Germany . |
| 3910635 | 4/1990 | Fed. Rep. of Germany . |
| 54-117486 | 9/1979 | Japan . |
| 63-258462 | 10/1988 | Japan . |
| 63-258463 | 10/1988 | Japan . |
| 63-258467 | 10/1988 | Japan . |
| 1290671 | 11/1989 | Japan . |
| 2-56469 | 2/1990 | Japan . |
| 3-31266 | 2/1991 | Japan . |
| 3-52873 | 3/1991 | Japan . |
| 3-128362 | 5/1991 | Japan . |
| 2237570 | 10/1990 | United Kingdom . |

OTHER PUBLICATIONS

March, Advanced Organic Chem. 3rd Edition, p. 445, Reaction O-119.
Derwent Abstract of DE-3,910,635 (Apr. 1990).

Primary Examiner—Cecilia Shen
Attorney, Agent, or Firm—Stevens, Davis, Miller & Mosher

[57] ABSTRACT

A herbicidal pyrimidine derivative having the formula,

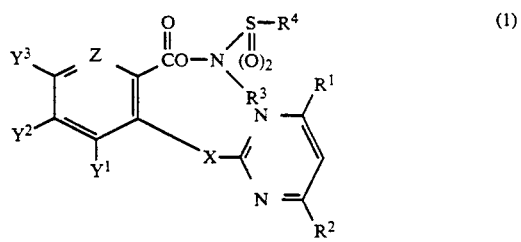

wherein $R^1$, $R^2$, $R^3$, $R^4$, $Y_1$, $Y_2$, $Y_3$, X and Z are defined as in the specification.

13 Claims, No Drawings

PYRIMIDINE DERIVATIVES

The present invention relates to a novel pyrimidine derivative, a method for producing the same, its use as a herbicide and an intermediate of the same.

European Patent Application No. 0223 406Al, 0249 708Al, etc. disclose that pyrimidine derivatives can be used as an active ingredient for herbicides.

However, these compounds are not always said to be satisfactory because they are insufficient in herbicidal activity.

On the other hand, a large number of herbicides for crop lands or non-crop lands are now in use. However, there are many kinds of weeds to be controlled and generation of the weeds extends over a long period of time, so that development of herbicides having a higher herbicidal activity and a broader herbicidal spectrum than before is being desired. Further, in recent years, no-till cultivation has been carried out for the purposes of saving labor, extending cultivation period, preventing soil erosion, etc. Therefore, it is being much desired to develop herbicides having both a high post-emergence herbicidal activity against weeds and pre-emergence herbicidal activity, their excellent-residual activity at high level, and a high selectivity to the undesired weeds as compared with the desired crops when crops are cultivated after application of herbicides.

In view of the situation like this, the present inventors have extensively studied, and as a result, have found that pyrimidine derivatives represented by the following formula (1) are compounds having an excellent herbicidal activity and having few foregoing defects, and that some of the derivatives have a high selectivity to the undesired weeds as compared with the desired crops. That is, the pyrimidine derivative can control the undesired weeds widely generated in crop lands or non-crop lands at low dosage rates, has a broad herbicidal spectrum and also can safely be used for no-till cultivation. The present invention is based on this finding.

According to the present invention, there are provided a pyrimidine derivative having the formula (hereinafter present compound),

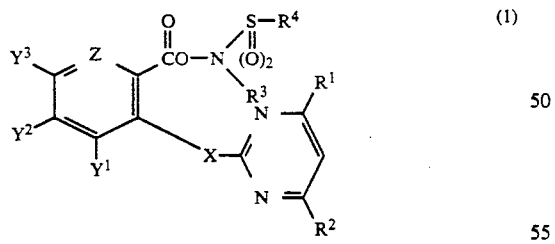

wherein
each of $R^1$ and $R^2$, which may be the same or different, is $C_1-C_6$ alkyl, $C_1-C_6$ alkoxy, halo $C_1-C_6$ alkoxy or halogen;
$R^3$ is hydrogen or $C_1-C_6$ alkyl;
$R^4$ is $C_1-C_6$ alkyl, halo $C_1-C_6$ alkyl, benzyl, phenyl or phenyl substituted with at least one member selected from the group consisting of $C_1-C_6$ alkyl, $C_1-C_6$ alkoxy, halo $C_1-C_6$ alkyl, $C_1-C_6$ alkoxycarbonyl, nitro and halogen;
X is oxygen or sulfur;
Z is nitrogen or $CY^4$;

each of $Y^1$, $Y^2$ and $Y^3$, which may be the same or different, is hydrogen, halogen, $C_1-C_6$ alkyl or $C_1-C_6$ alkoxy; and $Y^4$ is hydrogen, hydroxyl, mercapto, nitro, halogen, $C_1-C_6$ alkyl, $C_2-C_6$ alkyenyl, $C_2-C_6$ alkynyl, $C_1-C_6$ alkoxy, $C_3-C_6$ alkenyloxy, $C_3-C_6$ alkynyloxy, halo $C_1-C_6$ alkyl, halo $C_2-C_6$ alkenyl, halo $C_2-C_6$ alkynyl, halo $C_1-C_6$ alkoxy, halo $C_3-C_6$ alkenyloxy, halo $C_3-C_6$ alkynyloxy, $C_1-C_6$ alkoxy $C_1-C_6$ alkyl, $C_3-C_6$ alkenyloxy $C_1-C_6$ alkyl, $C_3-C_6$ aklynyloxy $C_1-C_6$ alkyl, cyano, formyl, carboxyl, $C_1-C_6$ alkoxycarbonyl, $C_3-C_6$ alkenyloxycarbonyl, $C_3-C_6$ alkynyloxycarbonyl, phenyl, phenyl substituted with at least one member selected from the group consisting of $C_1-C_6$ alkyl, $C_1-C_6$ alkoxy, halo $C_1-C_6$ alkyl, $C_1-C_6$ alkoxycarbonyl and halogen, phenoxy, phenoxy substituted with at least one member selected from the group consisting of $C_1-C_6$ alkyl, $C_1-C_6$ alkoxy, halo $C_1-C_6$ alkyl, $C_1-C_6$ alkoxycarbonyl and halogen, phenylthio, phenylthio substituted with at least one member selected from the group consisting of $C_1-C_6$ alkyl, $C_1-C_6$ alkoxy, halo $C_1-C_6$ alkyl, $C_1-C_6$ alkoxycarbonyl and halogen, benzyloxy, benzyloxy substituted with at least one member selected from the group consisting of $C_1-C_6$ alkyl, $C_1-C_6$ alkoxy, halo $C_1-C_6$ alkyl, $C_1-C_6$ alkoxycarbonyl and halogen, benzylthio, benzylthio substituted with at least one member selected from the group consisting of $C_1-C_6$ alkyl, $C_1-C_6$ alkoxy, halo $C_1-C_6$ alkyl, $C_1-C_6$ alkoxycarbonyl and halogen,

wherein each of $R^5$ and $R^6$, which may be the same or different, is hydrogen, $C_1-C_6$ alkyl, $C_3-C_6$ alkenyl or $C_3-C_6$ alkynyl,

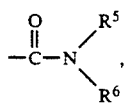

wherein $R^5$ and $R^6$ are as defined above,

wherein $R^7$ is $C_1-C_6$ alkyl, $C_3-C_6$ alkenyl or $C_3-C_6$ alkynyl and m is an integer of 0, 1 or 2,

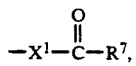

wherein $X^1$ is oxygen or sulfur, and $R^7$ is as defined above, or

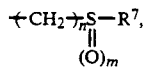

wherein $R^7$ and m are as defined above, and n is an integer of from 1 to 4;

a method for producing the pyrimidine derivative (1) which comprises reacting a compound having the formula,

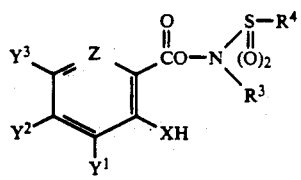
(2)

wherein $R^3$, $R^4$, X, Z, $Y^1$, $Y^2$ and $Y^3$ are as defined above, with a compound having the formula,

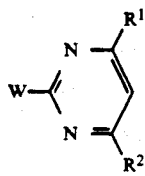
(3)

wherein each of $R^1$ and $R^2$ are as defined above; W is halogen or

wherein $R^8$ is $C_1$–$C_6$ alkyl, benzyl or benzyl substituted with at least one member selected from the group consisting of $C_1$–$C_6$ alkyl, $C_1$–$C_6$ alkoxy, halogen or nitro; and l is an integer of 0, 1 or 2;

a method for producing the pyrimidine derivative (1) which comprises the steps of (i) reacting a carboxylic acid derivative having the formula (4),

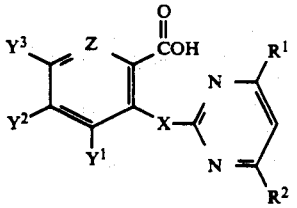
(4)

wherein X, Z, $Y^1$, $Y^2$, $Y^3$, $R^1$ and $R^2$ are as defined above, with an acid-halogenating agent or an active esterifying agent to obtain a reaction product; and (ii) reacting the reaction product with a sulfohydroxamic acid derivative having the formula,

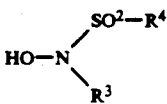
(5)

(wherein $R^3$ and $R^4$ are as defined above)
a method for producing the pyrimidine derivative (1) which comprises reacting a compound having the formula (6),

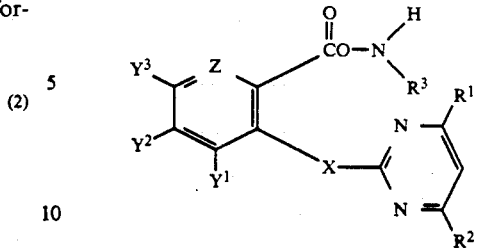
(6)

wherein X, Z, $Y^1$, $Y^2$, $Y^3$, $R^1$, $R^2$ and $R^3$ are as defined above, with a sulfonyl halide having the formula, $$W^3-SO_2-R^4 \qquad (7)$$

wherein $W^3$ is halogen; $R^4$ is as defined above, a compound having the formula,

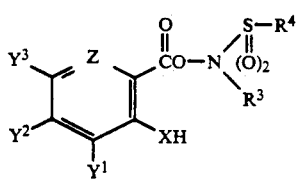
(2)

wherein $R^1$, $R^4$, X, Z, $Y^1$, $Y^2$ and $Y^3$ are as defined above; a herbicidal composition which comprises as an active ingredient a herbicidally effective amount of the pyrimidine derivative (1) described above, and an inert carrier or a diluent;
a method for controlling undesirable weeds, which comprises applying the above herbicidal composition to an area where undesirable weeds grow or are likely to grow; and
a use of the pyrimidine derivative (1) as a herbicide.

In the formula (1), examples of the $C_1$–$C_6$ alkyl group include methyl, ethyl, n-propyl, isopropyl, n-butyl, sec-butyl, tert-butyl, n-hexyl, etc; examples of the $C_1$–$C_6$ alkoxy group include methoxy, ethoxy, n-propoxy, isopropoxy, n-butoxy, hexyloxy, etc; and examples of the $C_1$–$C_6$ alkoxycarbonyl group include methoxycarbonyl, ethoxycarbonyl, n-butoxycarbonyl, hexyloxycarbonyl, etc.

The halogen atom in the formula (I) includes fluorine, chlorine, bromine and iodine.

Examples of the halo $C_1$–$C_6$ alkyl group include fluoromethyl, difluoromethyl, trifluoromethyl, 2-chloroethyl, 3-bromopropyl, etc.

When phenyl or a substituted phenyl group is selected as $R^4$, the examples thereof include phenyl, 2-methylphenyl, 3-ethylphenyl, 4-hexylphenyl, 2,6-dimethylphenyl, 3-methoxyphenyl, 4-isopropoxyphenyl, 3-hexyloxyphenyl, 2-trifluoromethylphenyl, 3-difluoromethylphenyl, 2-methoxycarbonylphenyl, 2-ethoxycarbonylphenyl, 2-n-propoxycarbonylphenyl, 2-hexyloxycarbonylphenyl, 2-fluorophenyl, 2=chlorophenyl, 3-bromophenyl, 2,4-dichlorophenyl, nitrophenyl etc.

When a halo $C_1$–$C_6$ alkoxy group is selected as $R^1$ or $R^2$, the examples thereof include fluoromethoxy, difluoromethoxy, trifluoromethoxy, etc.

When a $C_2$–$C_6$ alkenyl group is selected as $Y^4$, the examples thereof include vinyl, allyl, 1-butenyl, 2-butenyl, 3-butenyl, 3-pentenyl, 2-pentenyl, 2-hexenyl, etc.

When a $C_2$–$C_6$ alkynyl group is selected as $Y^4$, the examples thereof include ethynyl, propargyl, 1-butynyl, 2-butynyl, 2-pentynyl, 3-pentynyl, 2-hexynyl, etc.

When a $C_3$–$C_6$ alkenyloxy group is selected as $Y^4$, the examples thereof include allyloxy, 2-butenyloxy, 3-butenyloxy, 2-hexenyloxy, etc.

When a $C_3$–$C_6$ alkynyloxy group is selected as $Y^4$, the examples thereof include propargyloxy, 2-butynyloxy, 3-butynyloxy, 2-hexynyloxy, etc.

When a halo $C_6$–$C_6$ alkenyl group is selected as $Y^4$, the examples thereof include 1-chlorovinyl, 3-chloroallyl, 5-bromo-2-pentenyl, 6-iodo-2-hexenyl, 5,5,5-trifluoro-2-pentenyl, etc.

When a halo $C_2$–$C_6$ alkynyl group is selected as $Y^4$, the examples thereof include 2-iodoethynyl, 5-bromo-2-pentynyl, 6-iode-2-hexynyl, 5,5,5-trifluoro-2-pentynyl, etc.

When a halo $C_1$–$C_6$ alkoxy group is selected as $Y^4$, the examples thereof include fluoromethoxy, difluoromethoxy, trifluoromethyl, 1,1,2,2-tetrafluoroethoxy, etc.

When a halo $C_3$–$C_6$ alkenyloxy group is selected as $Y^4$, the examples thereof include 3-chloroallyloxy, 5-bromo-2-pentenyloxy, 6-iodo-2-hexenyloxy, 5,5,5-trifluoro-2-pentenyloxy, etc.

When a halo $C_3$–$C_6$ alkynyloxy group is selected as $Y^4$, the examples thereof include 5-bromo-2-pentynyloxy, 5-chloro-2-pentynyloxy, 1-iodo-2-hexynyloxy, 5,5,5-tritluoro-2-pentynyloxy, 3-iodopropargyloxy, etc.

When a $C_1$–$C_6$ alkoxy $C_1$–$C_6$ alkyl group is selected as $Y^4$, the examples thereof include methoxymethyl, ethoxymethyl, 2-methoxyethyl, 4-n-propoxybutyl, 2-n-butoxyethyl, 6-hexyloxyhexyl, etc.

When a $C_6$–$C_6$ alkenyloxy $C_1$–$C_6$ alkyl group is selected as $Y^4$, the examples thereof include allyloxymethyl, 2-allyloxyethyl, 4-allyloxybutyl, 3-(2-butenyloxy)propyl, 6-(hexenyloxy)hexyl, etc.

When a $C_6$–$C_6$ alkynyloxy $C_1$–$C_6$ alkyl group is selected as $Y^4$, the examples thereof include propargyloxymethyl, 2-propargyloxyethyl, 4-propargyloxybutyl, 3-(2-butynyloxy)propyl, 6-(2-hexynyloxy)hexyl, etc.

When a $C_6$–$C_6$ alkenyloxycarbonyl group is selected as $Y^4$, the examples thereof include allyloxycarbonyl, 2-butenyloxycarbonyl, 3-butenyloxycarbonyl, 2-hexenyloxycarbonyl, etc.

When a $C_3$–$C_6$ alkynyloxycarbonyl group is selected as $Y^4$, the examples thereof include propargyloxycarbonyl, 2-butynyloxycarbonyl, 3-butynyloxycarbonyl, 2-hexynyloxycarbonyl, etc.

When phenoxy or a substituted phenoxy group is selected as $Y^4$, the examples thereof include phenoxy, 2-methylphenoxy, 3-ethylphenoxy, 4-hexylphenoxy, 2,6-dimethylphenoxy, 3-methoxyphenoxy, 4-isopropoxyphenoxy, 3-hexyloxyphenoxy, 2-trifluoromethylphenoxy, 3-difluoromethylphenoxy, 2-methoxycarbonylphenoxy, 2-ethoxycarbonylphenoxy, 2-n-propoxycarbonylphenoxy, 2-hexyloxycarbonylphenoxy, 2-fluorophenoxy, 2-chlorophenoxy, 3-bromophenoxy, 2,4-dichlorophenoxy, etc.

When phenyl or a substituted phenyl group is selected as $Y^4$, the examples thereof include phenyl, 2-methylphenyl, 3-ethylphenyl, 4-hexylphenyl, 2,6-dimethylphenyl, 3-methoxyphenyl, 4-isopropoxyphenyl, 3-hexyloxyphenyl, 2-trifluoromethylphenyl, 3-difluoromethylphenyl, 2-methoxycarbonylphenyl, 2-ethoxycarbonylphenyl, 2-n-propoxycarbonylphenyl, 2-hexyloxycarbonylphenyl, 2-fluorophenyl, 2-chlorophenyl, 3-bromophenyl, 2,4-dichlorophenyl, etc.

When phenylthio or a substituted phenylthio group is selected as $Y^4$, the examples thereof include phenylthio, 2-methylphenylthio, 3-ethylphenylthio, 4-hexylphenylthio, 2,6-dimethylphenylthio, 3-methoxyphenylthio, 4-isopropoxyphenylthio, 3-hexyloxyphenylthio, 2-trifluoromethylphenylthio, 3-difluoromethylphenylthio, 2-methoxycarbonylphenylthio, 2-ethoxycarbonylphenylthio, 2-n-propoxycarbonylphenylthio, 2 -hexyloxycarbonylphenylthio, 2-fluorophenylthio, 2-chlorophenylthio, 3-bromophenylthio, 2,4-dichlorophenylthio, etc.

When benzyloxy or a substituted benzyloxy group is selected as $Y^4$, the examples thereof include benzyloxy, 2-methylbenzyloxy, 3-ethylbenzyloxy, 4-hexylbenzyloxy, 2,6-dimethylbenzyloxy, 3-methoxybenzyloxy, 4-isopropoxybenzyloxy, 3-hexyloxybenzyloxy, 2-trifluoromethylbenzyloxy, 3-difluoromethylbenzyloxy, 2-methoxycarbonylbenzyloxy, 2-ethoxycarbonylbenzyloxy, 2-n-propoxycarbonylbenzyloxy, 2-hexyloxycarbonylbenzyloxy 2-fluorobenzyloxy, 2-chlorobenzyloxy, 3-bromobenzyloxy, 2,4-dichlorobenzyloxy, etc.

When benzylthio or a substituted benzylthio group is selected as $Y^4$, the examples thereof include benzylthio, 2-methylbenzylthio, 3-ethylbenzylthio, 4-hexylbenzylthio, 2,6-dimethylbenzylthio, 3-methoxybenzylthio, 4-isopropoxybenzylthio, 3-hexyloxybenzylthio, 2-trifluoromethylbenzylthio, 3-difluoromethylbenzylthio, 2-methoxycarbonylbenzylthio, 2-ethoxycarboxylbenzylthio, 2-n-propoxycarbonylbenzylthio, 2-hexyloxycarbonylbenzylthio, 2-fluorobenzylthio, 2-chlorobenzylthio, 3-bromobenzylthio, 2,4-dichlorobenzylthio, etc.

When a $C_3$–$C_6$ alkenyl group is selected as $R^8$, $R^6$ or $R^7$, the examples thereof include allyl, 1-butenyl, 2-butenyl, 3-butenyl, 2-pentenyl, 3-pentenyl, 2-hexenyl, etc.

When a $C_3$–$C_6$ alkynyl group is selected as $R^8$, $R^6$ or $R^7$, the examples thereof include propargyl, 1-butynyl, 2-butynyl, 2-pentynyl, 3-pentynyl, 2-hexynyl, etc.

In the compound of the formula (1), the substituents $R^1$ and $R^2$, which may be the same or different, are preferably $C_1$–$C_6$ alkoxy, and more preferably, both of them are methoxy.

Z is preferably nitrogen or $CY^5$ wherein $Y^5$ is hydrogen, halogen, a halo $C_1$–$C_6$ alkyl group, a $C_1$–$C_6$ alkyl group, a $C_1$–$C_6$ alkoxy group, phenyl, phenyl substituted with at least one member selected from the group consisting of $C_1$–$C_6$ alkyl, $C_1$–$C_6$ alkoxy, halo $C_1$–$C_6$ alkyl, $C_1$–$C_6$ alkoxycarbonyl or halogen. More preferably, Z is nitrogen or $CY^5$ in which $Y^2$ is hydrogen or halogen. Most preferably Z is $CY^5$ and $Y^5$ is halogen.

$Y^1$ and $Y^2$, which may be the same or different, are preferably a hydrogen atom or a fluorine atom.

$Y^3$ is preferably hydrogen, fluorine or a $C_1$–$C_6$ alkoxy group. Specific examples of the pyrimidine derivative of the present invention include: 1-(4,6-dimethoxypyrimidin-2-yl)oxy-2-(N-methyl-N-methylsulfonylaminooxycarbonyl)benzene,

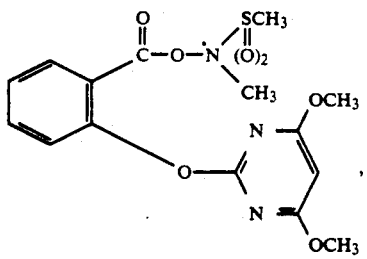

3-(4,6-dimethoxypyrimidin-2-yl)oxy-2-(N-methyl-N-methylsulfonylaminooxycarbonyl)pyridine,

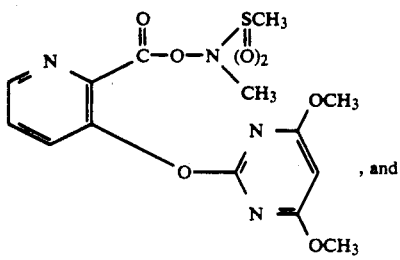

, and 1-chloro-3-(4,6-dimethoxypyrimidin-2-yl)oxy-2-(N-methyl-N-methylsulfonylaminooxycarbonyl)benzene,

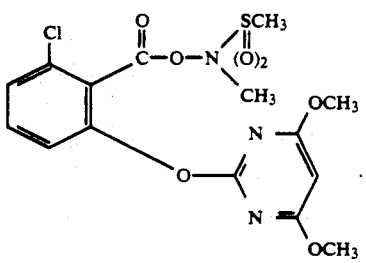

The present compound having the formula (1) in which Z is N and each of $R^1$ and $R^1$ is methoxy has a good selectivity to undesired weeds as compared with corn.

The present compound having the formula (1) in which Z is CCl, CF or CBr and each of $R^1$ and $R^2$ is methoxy has an excellent herbicidal activity and a good selectivity to undesired weeds as compared with cotton.

A method for producing the present compound is as follows.

The present compound (1) can be produced by reacting a compound represented by the formula (2),

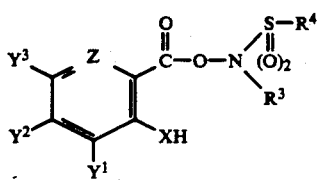

wherein $R^1$, $R^4$, X, $Y^1$, $Y^2$, $Y^3$ and Z are as defined above, with a compound represented by the formula (3),

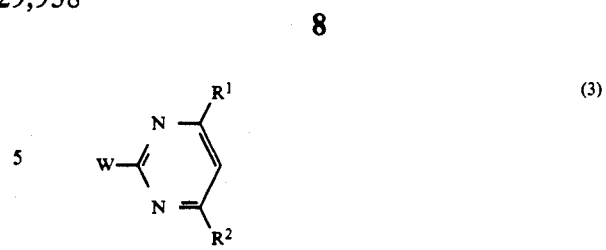

wherein $R^1$, $R^2$ and W are as defined above.

This reaction is usually carried out with or without a solvent in the presence of a base. The reaction temperature usually ranges from room temperature to the boiling point of the solvent, and the reaction time usually ranges from 10 minutes to 24 hours. Referring to the amounts of the reagents used for this reaction, the amount of the compound (3) is usually 1.0 to 1.5 equivalents based on 1 equivalent of the compound (2), and that of the base is usually 1.0 to 5.0 equivalents based on the same. The solvent includes aliphatic hydrocarbons (e.g. hexane, heptane, ligroin, petroleum ether), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, diethylene glycol dimethyl ether), ketones (e.g. acetone, methyl ethyl ketone, methyl isobutyl ketone, isophorone, cyclohexanone), alcohols (e.g. methanol, ethanol, isopropanol, tert-butanol, octanol, cyclohexanol, methyl cellosolve, diethylene glycol, glycerin), esters (e.g. ethyl formate, ethyl acetate, butyl acetate), nitro compounds (e.g. nitroethane, nitrobenzene), nitriles (e.g. acetonitrile, isobutyronitrile), tertiary amines (e.g. pyridine, triethylamine, N,N-diethylaniline, tributylamine, N-methylmorpholine), acid amides (e.g. formamide, N,N-dimethylformamide, acetamide), sulfur compounds (e.g. dimethyl sulfoxide, sulfolane), liquid ammonia, water and the mixtures thereof.

Specific examples of the base are organic bases (e.g. pyridine, triethylamine, N,N-diethylaniline), inorganic bases (e.g. sodium hydroxide, potassium hydroxide, sodium carbonate, potassium carbonate, sodium hydride), alkali metal alkoxides (e.g. sodium methoxide, sodium ethoxide), etc.

After completion of the reaction, the reaction solution may be after-treated as usual. That is, water is added to the solution which is then extracted with an organic solvent and concentrated, and if necessary, the product obtained is subjected to chromatography, distillation, recrystallization, etc. Thus, the desired present compound can be obtained.

The compound represented by the formula (3) can be produced according to Japanese Patent Application Kokai No. 63-23870, J. Org. Chem., 26, 792 (1961), etc.

The present compound can also be produced by reacting a compound represented by the formula (4),

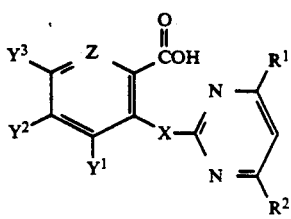

wherein $R^1$, $R^2$, X, $Y^1$, $Y^2$, $Y^3$ and Z are as defined above, with an acid-halogenating agent or an active esterifying agent (hereinafter reaction (i)), and reacting the resulting reaction product with a sulfohydroxamic acid derivative represented by the formula (5),

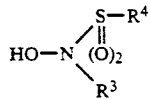
(5)

wherein $R^1$ and $R^4$ are as defined above (hereinafter reaction (ii)).

In the above reaction (i), specific examples of the acid-halogenating agent are thionyl chloride, thionyl bromide, phosphorus trichloride, phosphorus tribromide, phosphorus pentachloride, phosphorus oxychloride, phosgene, oxalic acid dichloride, etc. Specific examples of the active esterifying agent are N,N'-disubstituted carbodiimides such as N,N'-dicyclohexylcarbodiimide, N,N'-diisopropylcarbodiimide, 1-ethyl-3-(3-dimethylaminopropyl)carbodiimide hydrochloride, etc.; arylsulfonyl chlorides such as 2,4,6-trimethylbenzenesulfonyl chloride, 2,4,6-triisopropylbenzenesulfonyl chloride, etc.; N,N'-carbonyldiimidazole; diphenylphosphorylazide; N-ethoxycarbonyl-2-ethoxy-1,2-dihydroquinoline; N-ethyl-2'-hydroxybenzisoxazolium trifluoroborate; N-ethyl-5-phenylisoxazolium-3'-sulfonate; etc.

By this reaction, a compound represented by the formula (6),

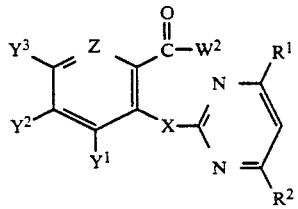
(8)

wherein $R^1$, $R^2$, X, $Y^1$, $Y^2$, $Y^3$ and Z are as defined above, is produced in the reaction system.

In the above formula (8), a substituent $W^2$ represents a halogen atom when the acid-halogenating agent was used; $W^2$ represents an N,N'-disubstituted-2-isoureido group when N,N'-disubstituted carbodiimide was used as the active esterifying agent; $W^2$ represents an arylsulfonyloxy group when arylsulfonyl chloride was used as said agent; $W^2$ represents an imidazolyl group when N,N'-carbonyldiimidazole was used as said agent; $W^2$ represents an azide group when diphenylphosphorylazide was used as said agent; $W^2$ represents an ethoxycarbonyloxy group when N-ethoxycarbonyl-2-ethoxy-1,2-dihydroquinoline was used as said agent; $W^2$ represents a 3-(N-ethylaminocarbonyl)-2-hydroxyphenoxy group when N-ethyl-2'-hydroxybenzisoxazolium trifluoroborate was used as said agent; and $W^2$ represents a group

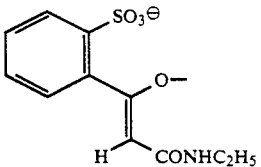

when N-ethyl-5-phenylisoxazolium-3'-sulfonate was used as said agent.

In the reaction system, $W^2$ can also take a form of acid anhydride containing the moiety represented by the formula,

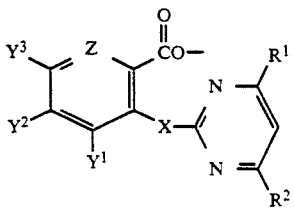

wherein $R^1$, $R^2$, X, $Y^1$, $Y^2$, $Y^3$ and Z are as defined above.

The amount of the foregoing acid-halogenating agent or active esterifying agent used is usually 1 to 10 equivalents based on 1 equivalent of the compound represented by the formula (4).

The amount of the sulfohydroxamic acid derivative of the formula (5) used is usually 1 to 5 equivalents based on 1 equivalent of the compound represented by the formula (4).

The reactions (i) and (ii) can also be carried out, if necessary, in the presence of a base. Such a base includes organic bases (e.g. 1-methylimidazole, 3-nitro-1H-1,2,4-triazole, 1H-tetrazole, 1H-1,2,4-triazole, imidazole, pyridine, triethylamine) and inorganic bases (e.g. potassium carbonate). The amount of the base used is usually 1 to 20 equivalents based on 1 equivalent of the compound represented by the formula (4).

The reactions (i) and (ii) are usually carried out in the presence of an inert solvent. Such a solvent includes aliphatic hydrocarbons (e.g. hexane, heptane, ligroin, petroleum ether), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, diethylene glycol dimethyl ether), ketones (e.g. acetone, methyl ethyl ketone, methyl isobutyl ketone, isophorone, cyclohexanone), esters (e.g. ethyl formate, ethyl acetate, butyl acetate), nitro compounds (e.g. nitroethane, nitrobenzene), nitriles (e.g. acetonitrile, isobutyronitrile), tertiary amines (e.g. pyridine, triethylamine, N,N-diethylaniline, tributylamine, N-methylmorpholine), acid amides (e.g. N,N-dimethylformamide), sulfur compounds (e.g. dimethyl sulfoxide, sulfolane) and the mixtures thereof.

Generally, the reaction temperature usually ranges from 0° C. to the boiling point of the solvent in any of the reactions (i) and (ii). The reaction time usually ranges from 1 to 24 hours for each reaction, and from about 1 to about 48 hours through the reactions (i) and (ii).

After completion of the reaction, the reaction solution may be after-treated as usual. That is, water is added to the solution which is then extracted with an organic solvent and concentrated, and if necessary, the product obtained is subjected to the chromatography, distillation, recrystallization, etc. Thus, the desired present compound can be obtained.

The present compound can also be prepared by reacting a compound represented by the formula (6), with a sulfonyl halide represented by the formula (7)

$$W^3-\underset{(O)_2}{\overset{}{S}}-R^4 \tag{7}$$

wherein $R^4$ and $W^3$ are as defined above.

This reaction is usually carried out with or without a solvent.

The reaction can also be carried out, if necessary, in the presence of a base. The reaction temperature usually ranges from room temperature to the boiling point of the solvent, and the reaction time usually ranges from 30 minutes to 24 hours. Referring to the amounts of the reagents used for this reaction, the amount of the halide (7) is usually 1.0 to 5.0 equivalents based on 1 equivalent of the compound (6), and that of the base is usually 1.0 to 10.0 equivalents based on the same. Examples of the solvent include aliphatic hydrocarbons (e.g. hexane, heptane, ligroin, petroleum ether), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, diethylene glycol dimethyl ether) and ketones (e.g. acetone, methyl ethyl ketone, methyl isobutyl ketone, isophorone, cyclohexanone), esters (e.g. ethyl formate, ethyl acetate, butyl acetate), nitro compounds (e.g. nitroethane, nitrobenzene), nitriles (e.g. acetonitrile, isobutyronitrile), tertiary amines (e.g. pyridine, triethylamine, N,N-diethylaniline, tributylamine, N-methylmorpholine), acid amides (e.g. formamide, N,N-dimethylformamide, acetamide), sulfur compounds (e.g. dimethyl sulfoxide, sulfolane), and mixtures thereof.

The base includes organic bases (e.g. pyridine, triethylamine, N,N-diethylaniline), inorganic bases (e.g. sodium hydroxide, potassium hydroxide, sodium carbonate, potassium carbonate, sodium hydride), alkali metal alkoxides (e.g. sodium methoxide, sodium ethoxide), etc.

After completion of the reaction, the reaction solution is after-treated as usual. That is, water is added to the solution which is then extracted with an organic solvent and concentrated, and if necessary, the product obtained is subjected to chromatography, distillation, recrystallization, etc. Thus, the desired present compound can be obtained.

The compound represented by the formula (4) can be produced according to EP 0 223 406 Al, etc.

The compound represented by the formula (6) can be produced according to EP 0 426 476.

The sulfohydroxamic acid derivative (5) can be produced by reacting a compound represented by the formula (11)

(11)

wherein $R^3$ is as defined above with a compound represented by the formula (12)

$$R^4-SO_2Cl \tag{12}$$

wherein $R^4$ is as described above, generally with a solvent such as tetrahydrofuran at room temperature.

In producing the present compounds, when the compound (a starting material for compound (1)), represented by the formula (2) is other than the compounds in which $Y^4$ is a group

in which $R^6$ is as defined above, or a group,

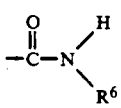

in which $R^6$ is as defined above, said compound can be produced as follows: The method comprises reacting an aromatic carboxylic acid halide represented by the following formula (9),

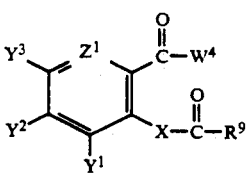
(9)

wherein X, $Y^1$, $Y^2$ and $Y^3$ are as defined above, $W^4$ represents a halogen atom, $R^9$ represents a $C_1-C_6$ alkyl group, and $Z^1$ represents $CY^{4'}$ wherein $Y^{4'}$ is hydrogen, nitro, halogen, $C_1-C_6$ alkyl, $C_2-C_6$ alkenyl, $C_2-C_6$ alkynyl, $C_1-C_6$ alkoxy, $C_3-C_6$ alkenyloxy, $C_3-C_6$ alkynyloxy, halo $C_1-C_6$ alkyl, halo $C_2-C_6$ alkenyl, halo $C_2-C_6$ alkynyl, halo $C_1-C_6$ alkoxy, halo $C_3-C_6$ alkenyloxy, halo $C_3-C_6$ alkynyloxy, $C_1-C_6$ alkoxy $C_1-C_6$ alkyl, $C_3-C_6$ alkenyloxy $C_1-C_6$ alkyl, $C_6-C_6$ alkynyloxy $C_1-C_6$ alkyl, cyano, formyl, carboxyl, $C_1-C_6$ alkoxycarbonyl, $C_3-C_6$ alkenyloxycarbonyl, $C_3-C_6$ alkynyloxycarbonyl, phenyl, phenyl substituted with at least one member selected from the group consisting of $C_1-C_6$ alkyl, $C_1-C_6$ alkoxy, halo $C_1-C_6$ alkyl, $C_1-C_6$ alkoxycarbonyl and halogen, phenoxy, phenoxy substituted with at least one member selected from the group consisting of $C_1-C_6$ alkyl, $C_1-C_6$ alkoxy, halo $C_1-C_6$ alkyl, $C_1-C_6$ alkoxycarbonyl and halogen, phenylthio, phenylthio substituted with at least one member selected from the group consisting of $C_1-C_6$ alkyl, $C_1-C_6$ alkoxy, halo $C_1-C_6$ alkyl, $C_1-C_6$ alkoxycarbonyl and halogen, benzyloxy, benzyloxy substituted with at least one member selected from the group consisting of $C_1-C_6$ alkyl, $C_1-C_6$ alkoxy, halo $C_1-C_6$ alkyl, $C_1-C_6$ alkoxycarbonyl and halogen, benzylthio, benzylthio substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl and halogen,

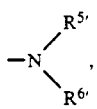

wherein each of $R^{5'}$ and $R^{6'}$, which may be the same or different, is $C_1$-$C_6$ alkyl, $C_3$-$C_6$ alkenyl or $C_3$-$C_6$ alkynyl,

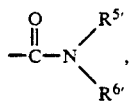

wherein $R^{5'}$ and $R^{6'}$ are as defined above,

wherein $R^7$ and m are as defined above,

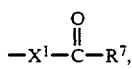

wherein $R^7$ and $X^1$ are as defined above, or

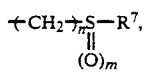

wherein $R^7$, m and n are as define-d above, or a group represented by the formula,

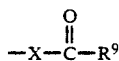

in which $R^9$ and X are as defined above, with the derivative represented by the formula (5) in the presence of a dehydrohalogenating agent and hydrolyzing the resulting compound with a base (e.g. sodium hydroxide, potassium hydroxide) or an acid (e.g. hydrochloric acid, sulfuric acid) to remove the group,

in which $R^9$ is as defined above.

The compound represented by the formula (2) can be produced by reacting an aromatic carboxylic acid derivative represented by the formula (10),

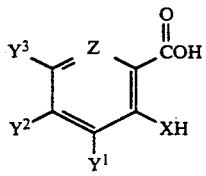

wherein X, $Y^1$, $Y^2$, $Y^3$ and Z are as defined above, with an acid-halogenating agent or an active esterifying agent (hereinafter reaction (iii)), and reacting the resulting reaction product with the sulfohydroxamic acid derivative represented by the formula (5) (hereinafter reaction (iv)).

The above reactions (iii) and (iv) can be carried out according to the foregoing reactions (i) and (ii), respectively. The aromatic carboxylic acid halide derivative (9) can be produced according to Beilstein H10/p.86, EI10/p.43, EII10/p.55, EIII10/p.151, EIV10/p.169, etc.

The aromatic carboxylic acid derivative (10) can be produced according to J. Org. Chem., 27, 3551 (1962), Chem. Pharm. Bull., 31, 407 (1983), Yakugaku Zasshi, 99, 657 (1979), Chem. Pharm. Bull., 27, 1468 (1979), J. Med. Chem., 21, 1093 (1978), Yakugaku Zasshi, 92, 1386 (1972), Eur. J. Med. Chem-Chim. Ther., 21, 379 (1986), J. Chem. Soc., Perkin Trans. 1, 2069 (1979), J. Chem. Soc., Perkin Trans.-1, 2079 (1979), J. Chem. Soc., Chem. Commun., 1127 (1968), J. Med. Chem., 31, 1039 (1988), Indian J. Chem., 25B, 796 (1986), J. Am. Chem. Soc., 107, 4593 (1985), J. Org. Chem., 50, 718 (1985), J. Agric. Food Chem., 32, 747 (1984), J. Pharm. Pharmacol., 35, 718 (1983), J. Org. Chem., 48, 1935 (1983), J. Chem. Soc., Chem. Commun., 1974, 362, etc.

Compound (1) includes its stereo isomer having a herbicidal activity.

Compound (2) includes its stereo isomer.

The present compounds (1) have an excellent herbicidal activity and some of them have an excellent selectivity to the undesired weeds as compared with the desired crops.

That is, the present compound, when used for foliar treatment and soil treatment in upland fields, exhibits a herbicidal activity against a wide variety of undesired weeds. Also, the present compound (1), when used for flooding treatment in paddy fields, exhibits a herbicidal activity against a wide variety of undesired weeds.

The present compound (1) can control a wide range of weeds generated in crop lands or non-crop lands, can be applied in low dosage rates, has a broad herbicidal spectrum and also can safely be used for no-till cultivation in soybean fields, peanut fields, corn fields, etc.

As weeds which can be controlled by the present compound, there are mentioned for example broad-leaved weeds such as wild buckwheat (*Polygonum convolvulus*), pale smartweed (*Polygonum lapathifolium*), common purslane (*Portulaca oleracea*), chickweed (*Stellaria media*), common lambsquarters (*Chenopodium album*), redroot pigweed (*Amaranthus retroflexus*), radish (*Raphanus sativus*), wild mustard (*Sinapis arvensis*), shepherds purse (*Capsella bursa-pastoris*), hemp sesbania (*sesbania exaltata*), sicklepod (*Cassia obtusifolia*), velvetleaf (*Abutilon theophrasti*), prickly sida (*Sida spinosa*), field pansy (*Viola arvensis*), cleavers (*Galium aparine*), ivyleaf morningglory (*Ipomoea hederacea*), tall morningglory (*Ipomoea purpurea*), field bindweed (*Convolvulus arvensis*), red deadnettle (*Lamium purpureum*), henbit (*Lamium amplexicaure*), jimsonweed (*Datura stramonium*), black nightshade (*Solanum niqrum*), birdseye speedwell (*Veronica persica*), cocklebur (*Xanthium strumarium*), sunflower (*Helianthus annuus*), scentless chamomile (*Matricaria perforata*), corn marigold (*Chrysanthemum segetum*), etc.; Gramineae weeds such as Japanese millet (*Echinochloa frumentacea*), barnyardgrass (*Echinochloa crus-qalli*), green foxtail (*Setaria viridis*), giant foxtail (*Setaria faberi*), large crabgrass (*Digitaria sanguinalis*), annual bluegrass (*Poa annua*), blackgrass (*Alopecurus myosuroides*), oat (*Avena sativa*), wild oat (*Avena fatua*), johnsongrass (*Sorghum halepense*), quackgrass (*Agropyron repens*), downy brome (*Bromus tectorum*), bermudagrass (*Cynodon dactylon*), etc.; Commelinaceae weeds-such as dayflower (*Commelina communis*), etc.; and Cyperaceae weeds such as rice flatsedge (*Cyperus iria*), purple nutsedge (*Cyperus rotundus*), etc. In addition, some of the present compounds give such no phytotoxicity as becoming a problem to main crops such as corn, wheat, barley, rice, soybean, cotton, beet, etc.

In flooding treatment in paddy fields, the present compounds exhibit a herbicidal activity against gramineous weeds such as barnyardgrass (*Echinochloa oryzicola*), etc.; broad-leaved weeds such as false pimpernel (*Lindernia procumbens*), indian toothcup (*Rotala indica*), waterwort (*Elatine triandra*), Ammannia multiflora, etc.; Cyperaceae weeds such as smallflower umbrellaplant (*Cyperus difformis*), bulrush (*Scirpus juncoides*), slender spikerush (*Eleocharis acicularis*), water nutgrass (*Cyperus serotinus*), etc.; monochoria (*Monochoria vaginalis*), arrowhead (*Sagittaria pyqmaea*), etc.

When the present compound (1) is used as an active ingredient for herbicides, it is usually formulated before use into emulsifiable concentrates, wettable powders, suspension formulations, granules, water-dispersible granules, etc. by mixing the present compound (1) with solid carriers, liquid carriers, surface active agents or other auxiliaries for formulation.

The content of the compound (1) as an active ingredient in these preparations is normally within a range of about 0.003 to 90% by weight, preferably of about 0.01 to 80% by weight.

Examples of the solid carriers are fine powders or granules of kaolin clay, attapulgite clay, bentonite, terra alba, pyrophyllite, talc, diatomaceous earth, calcite, walnut shell powders, urea, ammonium sulfate and synthetic hydrated silicon dioxide, etc.

Examples of the liquid carriers are aromatic hydrocarbons (e.g. xylene, methylnaphthalene), alcohols (e.g. isopropanol, ethylene glycol, cellosolve), ketones (e.g. acetone, cyclohexanone, isophorone), vegetable oils (soybean oil, cotton seed oil), dimethyl sulfoxide, N,N-dimethylformamide, acetonitrile, water, etc.

Examples of the surface active agents used for emulsification, dispersion or spreading, etc. are anionic surface active agents such as salts of alkyl sulfates, alkylsulfonates, alkylarylsulfonates, dialkyl sulfosuccinates, salts of polyoxyethylene alkylaryl ether phosphoric acid esters, etc., and nonionic surface active agents such as polyoxyethylene alkyl ethers, polyoxyethylene alkylaryl ethers, polyoxyethylene polyoxypropylene block copolymers, sorbitan fatty acid esters, polyoxyethylene sorbitan fatty acid esters, etc.

Examples of the other auxiliaries for formulation are lignosulfonates, alginates, polyvinyl alcohol, gum arabic, CMC (carboxymethyl cellulose), PAP (isopropyl acid phosphate), etc.

The present compound (1) is usually formulated into an appropriate formulation and used in soil treatment, foliar treatment or flooding treatment before or after emergence of weeds. The soil treatment includes soil surface treatment and soil incorporation treatment. The foliar treatment includes, in addition to the treatments of plants mentioned above, direct treatment in which the formulation is applied only to weeds so as to prevent the formulation from adhering to crops.

The herbicidal activity of the present compound (1) can be expected to be increased by using the compound in mixture with other herbicides. Further, the present compound (1) can also be used in mixture with insecticides, acaricides, nematocides, fungicides, plant growth regulators, fertilizers, soil improvers, etc.

The present compound (1) can be used as an active ingredient for herbicides used in paddy field, ridges of paddy fields, plowed fields, fields other than plowed fields, orchards, pastures, turfs, forests and fields other than agricultural fields, etc.

When the present compound (1) is used as an active ingredient for herbicides, the dosage rate varies depending upon the weather conditions, preparation forms, when, how and where the treatment is carried out, weeds species to be controlled, crops species to be protected, etc. Usually, however, the dosage rate is from 0.01 grams to 100 grams of the active ingredient per are, preferably from 0.03 grams to 80 grams of the active ingredient per are.

The herbicidal composition of the invention formulated in the form of an emulsifiable concentrate, a wettable powder or a suspension formulations may ordinarily be employed after diluting it with water at a volume of about 1 to 10 liters per are. If necessary, auxiliaries such as a spreading agent are added to the water. The granules are usually applied as they are without being diluted.

Examples of the spreading agent are, in addition to the foregoing surface active agents, substances such as polyoxyethylene resin acids (esters), lignosulfonates, abietates, dinaphthylmethanedisulfonates, paraffin, etc.

The present invention will be illustrated in more detail with reference to the following production examples, formulation examples and test examples, which are not however to be interpreted as limiting the invention thereto.

First, production examples for the present compound (1) are shown.

PRODUCTION EXAMPLE 1

1.10 Grams of 2-(4,6-dimethoxypyrimidin-2-yl)oxybenzoic acid, 0.50 g of N-methylmethanesulfohydroxamic acid and 1.45 g of 2,4,6-triisopropylbenzenesulfonyl chloride were dissolved in 15 ml of tetrahydrofuran, and 0.98 g of 1-methylimidazole was added thereto. After stirring at room temperature for 3 hours, the reaction solution was poured into water and extracted with ethyl acetate. The organic layer was washed with water and dried over anhydrous magnesium sulfate. The solvent was removed under reduced pressure, and the residue obtained was subjected to thin layer chromatography (n-hexane-ethyl acetate/9:1 (v/v)) to obtain 0.88 g of 2-(4,6-dimethoxypirimidin-2-yl)oxy-1-(N-methyl-N-methylsulfonylaminooxycarbonyl)benzene [present compound (25)].

$^1$H-NMR (CDCl$_3$) δ: 2.95 (s, 3H), 3.01 (s, 3H), 3.75 (s, 6H), 5.72 (s, 1H), 7.10-8.03 (m, 4H).

m.p. 70°-71° C.

PRODUCTION EXAMPLE 2

Using the procedure shown in Production Example 1, 6-fluoro-2-(4,6-dimethoxypyrimidin-2-yl)oxy-1-(N-methyl-N-methylsulfonylaminooxycarbonyl)benzene (present compound (14)) can be obtained by reacting 1.12 g of 6-fluoro-2-(4,6-dimethoxypyrimidin-2-yl)oxybenzoic acid, 0.50 g of N-methylmethanesulfohydroxamic acid, 1.45 g of 2,4,6-triisopropylbenzenesulfonyl chloride and 0.98 g of 1-methylimidazole.

PRODUCTION EXAMPLE 3

Using the procedure shown in Production Example 1, 6-phenyl-2-(4,6-dimethoxypyrimidin-2-yl)oxy-1-(N-methyl-N-methylsulfonylaminooxycarbonyl)benzene (present compound (19)) can be obtained by reacting 1.41 g of 6-phenyl-2-(4,6-dimethoxypyrimidin-2-yl)oxybenzoic acid, 0.50 g of N-methylmethanesulfohydroxamic acid, 1.45 g of 2,4,6-triisopropylbenzenesulfonyl chloride and 0.98 g of 1-methylimidazole.

PRODUCTION EXAMPLE 4

Using the procedure shown in Production Example 1, 6-methoxy-2-(4,6-dimethoxypyrimidin-2-yl)oxy-1-(N-methyl-N-methylsulfonylaminooxycarbonyl)benzene (present compound (21)) can be obtained by reacting 1.22 g of 6-methoxy-2-(4,6-dimethoxypyrimidin-2-yl)oxybenzoic acid, 0.50 g of N-methylmethanesulfohydroxamic acid, 1.45 g of 2,4,6-triisopropylbenzenesulfonyl chloride and 0.98 g of 1-methylimidazole.

PRODUCTION EXAMPLE 5

Using the procedure shown in Production Example 1, 6-methyl-2-(4,6-dimethoxypyrimidin-2-yl)oxy-1-(N-methyl-N-methylsulfonylaminooxycarbonyl)benzene (present compound (16)) can be obtained by reacting 1.16 g of 6-methyl-2-(4,6-dimethoxypyrimidin-2-yl)oxybenzoic acid, 0.50 g of N-methylmethanesulfohydroxamic acid, 1.45 g of 2,4,6-triisopropylbenzenesulfonyl chloride and 0.98 g of 1-methylimidazole.

PRODUCTION EXAMPLE 6

Using the procedure shown in Production Example 1, 6-trifluoromethyl-2-(4,6-dimethoxypyrimidin-2-yl)oxy-1-(N-methyl-N-methylsulfonylaminooxycarbonyl)benzene (present compound (15)) can be obtained by reacting 1.38 g of 6-trifluoromethyl-2-(4,6-dimethoxypyrimidin-2-yl)oxybenzoic acid, 0.50 g of N-methylmethanesulfohydroxamic acid, 1.45 g of 2,4,6-triisopropylbenzenesulfonyl chloride and 0.98 g of 1-methylimidazole.

Table 1 illustrates specific examples of the compound (1), which can be produced by using the corresponding starting compounds.

TABLE 1

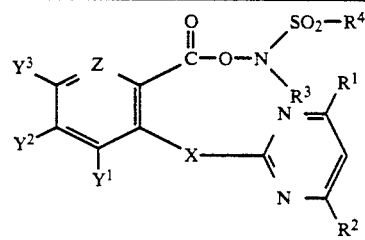

| Compound No. | $R^3$ | $R^4$ | $Y^1$ | $Y^2$ | $Y^3$ | X | Z | $R^1$ | $R^2$ | Physical properties (m.p., refractive index) |
|---|---|---|---|---|---|---|---|---|---|---|
| (1) | H | —⟨phenyl⟩ | H | H | H | O | CH | OCH$_3$ | OCH$_3$ | $n_D^{24.5}$ 1.5698 |
| (2) | H | CH$_3$ | H | H | H | O | CF | OCH$_3$ | OCH$_3$ | |
| (3) | H | CH$_3$ | H | H | H | O | CCl | OCH$_3$ | OCH$_3$ | |
| (4) | H | CH$_3$ | H | H | H | S | CCl | OCH$_3$ | OCH$_3$ | |
| (5) | H | CH$_3$ | H | H | H | O | CBr | OCH$_3$ | OCH$_3$ | |
| (6) | H | CH$_3$ | H | H | H | S | CBr | OCH$_3$ | OCH$_3$ | |
| (7) | CH$_3$ | CH$_3$ | H | H | H | O | CH | Cl | OCH$_3$ | |
| (8) | CH$_3$ | CH$_3$ | H | H | H | O | N | CH$_3$ | CH$_3$ | |
| (9) | CH$_3$ | CH$_3$ | H | H | H | O | CCl | OCH$_3$ | CH$_3$ | |
| (10) | CH$_3$ | CH$_3$ | H | H | H | S | CCl | OCH$_3$ | OCH$_3$ | |
| (11) | CH$_3$ | CH$_3$ | H | H | H | O | CBr | OCH$_3$ | OCH$_3$ | |
| (12) | CH$_3$ | —⟨C$_6$H$_4$-CH$_3$⟩ | H | H | H | O | CH | OCH$_3$ | OCH$_3$ | m.p. 149–150° C. |
| (13) | CH$_3$ | —⟨C$_6$H$_4$-CH$_3$⟩ | H | H | F | O | CH | OCH$_3$ | OCH$_3$ | $n_D^{22}$ 1.5508 |
| (14) | CH$_3$ | CH$_3$ | H | H | H | O | CF | OCH$_3$ | OCH$_3$ | |
| (15) | CH$_3$ | CH$_3$ | H | H | H | O | CCF$_3$ | OCH$_3$ | OCH$_3$ | |
| (16) | CH$_3$ | CH$_3$ | H | H | H | O | CCH$_3$ | OCH$_3$ | OCH$_3$ | |
| (17) | CH$_3$ | CH$_3$ | H | H | H | O | CNO$_2$ | OCH$_3$ | OCH$_3$ | |
| (18) | CH$_3$ | CH$_3$ | H | H | H | S | CF | OCH$_3$ | OCH$_3$ | |
| (19) | CH$_3$ | CH$_3$ | H | H | H | O | CC$_6$H$_5$ | OCH$_3$ | OCH$_3$ | |
| (20) | CH$_3$ | CH$_3$ | H | H | H | S | CCF$_3$ | OCH$_3$ | OCH$_3$ | |
| (21) | CH$_3$ | CH$_3$ | H | H | H | O | COCH$_3$ | OCH$_3$ | OCH$_3$ | |
| (22) | CH$_3$ | CH$_3$ | H | H | H | O | CC$_2$H$_5$ | OCH$_3$ | OCH$_3$ | |

TABLE 1-continued

| Compound No. | R³ | R⁴ | Y¹ | Y² | Y³ | X | Z | R¹ | R² | Physical properties (m.p., refractive index) |
|---|---|---|---|---|---|---|---|---|---|---|
| (23) | $CH_3$ | $CH_3$ | H | H | F | O | CCl | $OCH_3$ | $OCH_3$ | |
| (24) | $CH_3$ | 4-$CH_3$-$C_6H_4$ | H | H | Cl | O | CH | $OCH_3$ | $OCH_3$ | m.p. 146–147° C. |
| (25) | $CH_3$ | $CH_3$ | H | H | H | O | CH | $OCH_3$ | $OCH_3$ | m.p. 70–71° C. |
| (26) | H | $C_2H_5$ | H | H | $OCH_3$ | O | CCl | $OCH_3$ | $OCH_3$ | |
| (27) | H | $C_2H_5$ | H | H | H | O | CBr | $OCH_3$ | $OCH_3$ | |
| (28) | H | $C_3H_7(i)$ | H | H | H | S | CBr | $OCH_3$ | $OCH_3$ | |
| (29) | H | $C_3H_7(i)$ | H | H | H | O | $COCH_3$ | $OCH_3$ | $OCH_3$ | |
| (30) | H | $C_6H_{13}(n)$ | H | H | H | O | CCl | $OCH_3$ | $OCH_3$ | |
| (31) | $CH_3$ | $C_2H_5$ | H | H | H | O | N | $OCH_3$ | $OCH_3$ | |
| (32) | $CH_3$ | $C_2H_5$ | H | H | H | O | CF | $OCH_3$ | $OCH_3$ | |
| (33) | $CH_3$ | $C_2H_5$ | H | H | H | O | CCl | $OCH_3$ | $OCH_3$ | |
| (34) | $CH_3$ | $C_3H_7(i)$ | H | H | H | S | CCl | $OCH_3$ | $OCH_3$ | |
| (35) | $CH_3$ | $C_3H_7(i)$ | H | H | H | O | CBr | $OCH_3$ | $OCH_3$ | |
| (36) | $CH_3$ | $CH_3$ | H | H | H | O | N | $OCH_3$ | $OCH_3$ | $n_D^{22}$ 1.5283 |
| (37) | $CH_3$ | 2-Cl-$C_6H_4$ | H | H | H | O | CH | $OCH_3$ | $OCH_3$ | glassy |
| (38) | H | 4-$CH_3$-$C_6H_4$ | H | H | H | O | CCl | $OCH_3$ | $OCH_3$ | |
| (39) | $CH_3$ | $C_6H_{13}(n)$ | H | H | H | O | CCl | $OCH_3$ | $OCH_3$ | |
| (40) | $CH_3$ | $C_6H_5$ | H | H | H | O | N | $OCH_3$ | $OCH_3$ | |
| (41) | $CH_3$ | $C_6H_5$ | H | H | H | O | CCl | $OCH_3$ | $OCH_3$ | |
| (42) | $CH_3$ | 2-$CH_3$-$C_6H_4$ | H | H | H | S | CCl | $OCH_3$ | $OCH_3$ | |
| (43) | $CH_3$ | 4-$C_2H_5$-$C_6H_4$ | H | H | H | O | CBr | $OCH_3$ | $OCH_3$ | |
| (44) | $CH_3$ | 3-$C_6H_{13}(n)$-$C_6H_4$ | H | H | H | S | CBr | $OCH_3$ | $OCH_3$ | |

TABLE 1-continued

[Structure: Y³, Z, C(=O)-O-N(SO₂-R⁴)(R³) connected to a pyrimidine ring with R¹, R², X linker, Y¹, Y² substituents]

| Compound No. | R³ | R⁴ | Y¹ | Y² | Y³ | X | Z | R¹ | R² | Physical properties (m.p., refractive index) |
|---|---|---|---|---|---|---|---|---|---|---|
| (45) | CH₃ | 4-OCH₃-phenyl | H | H | H | O | COCH₃ | OCH₃ | OCH₃ | |
| (46) | CH₃ | 2-OC₂H₅-phenyl | H | H | H | O | CCl | OCH₃ | OCH₃ | |
| (47) | CH₃ | 3-OC₆H₁₃(n)-phenyl | H | H | H | O | CF | OCH₃ | OCH₃ | |
| (48) | CH₃ | 2-Cl-phenyl | H | H | H | O | CF | OCH₃ | OCH₃ | $n_D^{25}$ 1.5495 |
| (49) | CH₃ | CH₃ | H | H | H | O | CCl | OCH₃ | OCH₃ | $n_D^{22}$ 1.5378 |
| (50) | CH₃ | 3-F-phenyl | H | H | H | S | CCl | OCH₃ | OCH₃ | |
| (51) | CH₃ | 4-Cl-phenyl | H | H | H | O | CCH₃ | OCH₃ | OCH₃ | |
| (52) | CH₃ | 4-Br-phenyl | H | H | H | O | CCF₃ | OCH₃ | OCH₃ | |
| (53) | CH₃ | 2,4,5-trichlorophenyl | H | H | H | O | COCH₃ | OCH₃ | OCH₃ | |
| (54) | CH₃ | 2-CF₃-phenyl | H | H | H | O | CCl | OCH₃ | OCH₃ | |

TABLE 1-continued

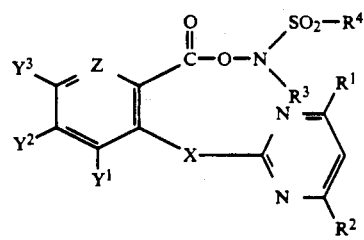

| Compound No. | R³ | R⁴ | Y¹ | Y² | Y³ | X | Z | R¹ | R² | Physical properties (m.p., refractive index) |
|---|---|---|---|---|---|---|---|---|---|---|
| (55) | CH₃ | 2-nitrophenyl | H | H | H | O | CH | OCH₃ | OCH₃ | |
| (56) | CH₃ | 2-(COOCH₃)phenyl | H | H | H | O | N | OCH₃ | OCH₃ | |
| (57) | CH₃ | 3-chloro-4-nitrophenyl | H | H | H | O | CCl | OCH₃ | OCH₃ | |
| (58) | CH₃ | 2,4,6-trimethylphenyl | H | H | H | S | CCl | OCH₃ | OCH₃ | |
| (59) | CH₃ | 3-(CF₃)phenyl | H | H | H | O | CBr | OCH₃ | OCH₃ | |
| (60) | CH₃ | 4-methylphenyl | H | H | OCH₃ | O | CH | OCH₃ | OCH₃ | glassy |
| (61) | C₂H₅ | CH₃ | H | H | H | O | CF | OCH₃ | OCH₃ | |
| (62) | C₂H₅ | CH₃ | H | H | H | O | CCl | OCH₃ | OCH₃ | |
| (63) | C₃H₇(i) | CH₃ | H | H | H | O | CCl | OCH₃ | OCH₃ | |
| (64) | C₆H₁₃(n) | CH₃ | H | H | H | O | CCl | OCH₃ | OCH₃ | |
| (65) | CH₃ | CH₃ | H | H | H | O | 2-methylphenyl-C | OCH₃ | OCH₃ | |
| (66) | CH₃ | CH₃ | H | H | H | O | 3-methoxyphenyl-C | OCH₃ | OCH₃ | |

TABLE 1-continued

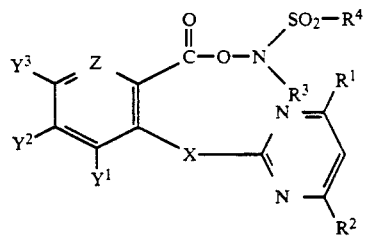

| Compound No. | R³ | R⁴ | Y¹ | Y² | Y³ | X | Z | R¹ | R² | Physical properties (m.p., refractive index) |
|---|---|---|---|---|---|---|---|---|---|---|
| (67) | CH₃ | CH₃ | H | H | H | O | C-C₆H₄-F (4-F) | OCH₃ | OCH₃ | |
| (68) | CH₃ | CH₃ | H | H | H | O | C-C₆H₄-COOCH₃ (2-COOCH₃) | OCH₃ | OCH₃ | |
| (69) | CH₃ | CH₃ | H | H | H | O | C-C₆H₄-CF₃ (3-CF₃) | OCH₃ | OCH₃ | |
| (70) | CH₃ | CH₃ | H | H | H | O | C-C₆H₃(Cl)(Cl) (2,4-diCl) | OCH₃ | OCH₃ | |

Production Examples for the compound (2), a starting material, are shown below.

PRODUCTION EXAMPLE 7

1.73 Grams of 6-chlorosalycilic acid is dissolved in 20 ml of tetrahydrofuran, 1.95 Grams of N,N'-carbonyldiimidazole is added to this solution. After stirring for 30 minutes at room temperature, 1.50 g of N-methyl-N-methylsulfonylhydroxylamine is added thereto. The resulting solution is stirred for 7 hours at room temperature, the reaction solution is poured into water, and extracted with ethyl acetate. The organic layer is washed with saturated sodium chloride solution and dried over anhydrus magnesium sulfate. The solvent is removed under reduced pressure, and the residue obtained is subjected to sillica gel chromatography to obtain 3-chloro-2-(N-methyl-N-methylsulfonylaminooxycarbonyl)phenol.

Table 2 illustrates specific examples of the compound (2), which can be produced by using the corresponding starting materials.

TABLE 2

| R³ | R⁴ | Y¹ | Y² | Y³ | X | Z |
|---|---|---|---|---|---|---|
| H | C₆H₅ | H | H | H | O | CH |
| H | CH₃ | H | H | H | O | CF |
| H | CH₃ | H | H | H | O | CCl |
| H | CH₃ | H | H | H | S | CCl |
| H | CH₃ | H | H | H | O | CBr |
| H | CH₃ | H | H | H | S | CBr |
| CH₃ | CH₃ | H | H | H | O | CH |
| CH₃ | CH₃ | H | H | H | O | N |
| CH₃ | CH₃ | H | H | H | O | CCl |
| CH₃ | CH₃ | H | H | H | S | CCl |
| CH₃ | CH₃ | H | H | H | O | CBr |
| CH₃ | 4-CH₃-C₆H₄ | H | H | H | O | CH |
| CH₃ | 4-CH₃-C₆H₄ | H | H | F | O | CH |
| CH₃ | CH₃ | H | H | H | O | CF |
| CH₃ | CH₃ | H | H | H | O | CCF₃ |
| CH₃ | CH₃ | H | H | H | O | CCH₃ |

TABLE 2-continued

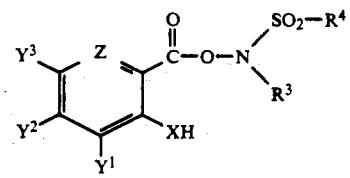

| R³ | R⁴ | Y¹ | Y² | Y³ | X | Z |
|---|---|---|---|---|---|---|
| CH₃ | CH₃ | H | H | H | O | CNO₂ |
| CH₃ | CH₃ | H | H | H | S | CF |
| CH₃ | CH₃ | H | H | H | O | CC₆H₅ |
| CH₃ | CH₃ | H | H | H | S | CCF₃ |
| CH₃ | CH₃ | H | H | H | O | COCH₃ |
| CH₃ | CH₃ | H | H | H | O | CC₂H₅ |
| CH₃ | CH₃ | H | H | F | O | CCl |
| CH₃ | 4-CH₃-C₆H₄ | H | H | Cl | O | CH |
| H | C₂H₅ | H | H | OCH₃ | O | CCl |
| H | C₂H₅ | H | H | H | O | CBr |
| H | C₃H₇(i) | H | H | H | S | CBr |
| H | C₃H₇(i) | H | H | H | O | COCH₃ |
| H | C₆H₁₃(n) | H | H | H | O | CCl |
| CH₃ | C₂H₅ | H | H | H | O | N |
| CH₃ | C₂H₅ | H | H | H | O | CF |
| CH₃ | C₂H₅ | H | H | H | O | CCl |
| CH₃ | C₃H₇(i) | H | H | H | S | CBr |
| CH₃ | C₃H₇(i) | H | H | H | O | CCl |
| CH₃ | 2-Cl-C₆H₄ | H | H | H | O | CH |
| H | 4-CH₃-C₆H₄ | H | H | H | O | CCl |
| CH₃ | C₆H₁₃(n) | H | H | H | O | CCl |
| CH₃ | C₆H₅ | H | H | H | O | N |
| CH₃ | C₆H₅ | H | H | H | O | CCl |
| CH₃ | 2-CH₃-C₆H₄ | H | H | H | S | CCl |
| CH₃ | 4-C₂H₅-C₆H₄ | H | H | H | O | CBr |
| CH₃ | 4-C₆H₁₃(n)-C₆H₄ | H | H | H | S | CBr |
| CH₃ | 4-OCH₃-C₆H₄ | H | H | H | O | COCH₃ |
| CH₃ | 2-OC₂H₅-C₆H₄ | H | H | H | O | CCl |
| CH₃ | 4-C₆H₁₃(n)-C₆H₄ | H | H | H | O | CF |
| CH₃ | 2-Cl-C₆H₄ | H | H | H | O | CF |
| CH₃ | 3-F-C₆H₄ | H | H | H | S | CCl |
| CH₃ | 4-Cl-C₆H₄ | H | H | H | O | CCH₃ |
| CH₃ | 4-Br-C₆H₄ | H | H | H | O | CCF₃ |
| CH₃ | 3,4,5-Cl₃-C₆H₂ | H | H | H | O | COCH₃ |
| CH₃ | 2-CF₃-C₆H₄ | H | H | H | O | CCl |
| CH₃ | 2-NO₂-C₆H₄ | H | H | H | O | CH |
| CH₃ | 2-COOCH₃-C₆H₄ | H | H | H | O | N |
| CH₃ | 3-Cl-4-NO₂-C₆H₃ | H | H | H | O | CCl |
| CH₃ | 2,4,6-(CH₃)₃-C₆H₂ | H | H | H | S | CCl |
| CH₃ | 3-CF₃-C₆H₄ | H | H | H | O | CBr |
| CH₃ | 4-CH₃-C₆H₄ | H | H | OCH₃ | O | CH |
| C₂H₅ | CH₃ | H | H | H | O | CF |
| C₂H₅ | CH₃ | H | H | H | O | CCl |
| C₃H₇(i) | CH₃ | H | H | H | O | CCl |
| C₆H₁₃(n) | CH₃ | H | H | H | O | CCl |

TABLE 2-continued

![structure with Y3, Y2, Y1, Z, C(=O)-O-N(R3)(SO2-R4), XH]

| R³ | R⁴ | Y¹ | Y² | Y³ | X | Z |
|---|---|---|---|---|---|---|
| CH₃ | CH₃ | H | H | H | O | C-phenyl-H₃C (with CH₃ substituent) |
| CH₃ | CH₃ | H | H | H | O | C-phenyl-OCH₃ |
| CH₃ | CH₃ | H | H | H | O | C-phenyl-F |
| CH₃ | CH₃ | H | H | H | O | C-phenyl-COOCH₃ |
| CH₃ | CH₃ | H | H | H | O | C-phenyl-CF₃ |
| CH₃ | CH₃ | H | H | H | O | C-phenyl-Cl,Cl |

Production Examples for the sulfohydroxamic acid derivative (5), a starting material, are shown below.

PRODUCTION EXAMPLE 8

5.02 Grams of N-methylhydroxylamine.HCl was suspended with 70 ml of tetrahydrofuran and 6.70 g of triethylamine was added to the solution. After stirring at room temperature for 0.5 hour, 5.73 g of p-toluenesulfonyl chloride was added to the reaction solution and stirred at room temperature over night. The saturated sodium chloride solution was added to the reaction solution and extracted with ethyl acetate. The organic layer was washed with saturated sodium chloride solution and dried over anhydrous magnesium sulfate. The solvent was removed under reduced pressure, and N-methyl-N-(p-toluenesulfonyl)hydroxylamine was obtained.

¹H-NMR (CDCl₃) δ: 2.43 (s, 3H), 2.79 (s, 3H), 7.32 (d, 2H, J=10.0 Hz), 7.45 (bs, 1H), 7.76 (d, 2H, J=10.0 Hz).

PRODUCTION EXAMPLE 9

Using the procedure shown in Production Example 8 starting from 2.51 g of N-methylhydroxylamine.HCl, 1.72 g of methanesulfonylchloride and 3.04 g of triethylamine gave

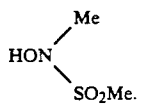

¹H-NMR (CDCl₃) δ: 2.93 (s, 3H), 3.01 (s, 3H), 7.71 (bs, 1H).

PRODUCTION EXAMPLE 10

Using the procedure shown in Production Example 8 starting from 8.35 g of N-methylhydroxylamine.HCl, 10.55 g of o-benzenesulfonylchloride and 11.1 g of triethylamine gave

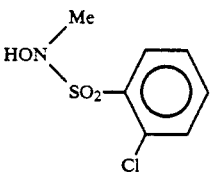

¹H-NMR (CDCl₃) δ: 3.02 (s, 3H), 6.95 (bs, 1H), 7.26-8.15 (m, 4H).

Formulation Examples are shown below. In the examples, the present compound (1) is shown by Compound No. in Table, and parts are by weight.

FORMULATION EXAMPLE 1

Fifty parts of any one of the present compounds (12), (24), (25), (37) and (60), 3 parts of calcium lignosulfonate, 2 parts of sodium lauryl sulfate and 45 parts of synthetic hydrated silicon dioxide are well mixed while being powdered to obtain a wettable powder.

FORMULATION EXAMPLE 2

Ten parts of any one of the present compounds (1), (12), (13), (24), (25), (36), (37), (48), (49) and (60), 14 parts of polyoxyethylene styrylphenyl ether, 6 parts of calcium dodecylbenzenesulfonate, 40 parts of xylene and 30 parts of cyclohexanone are well mixed to obtain an emulsifiable concentrate.

FORMULATION EXAMPLE 3

Two parts of any one of the present compounds (1), (12), (13), (24), (25), (36), (37), (48), (49) and (60), 1 part of synthetic hydrated silicon dioxide, 2 parts of calcium lignosulfonate, 30 parts of bentonite and 65 parts of kaolin clay are well pulverized and mixed. The resulting mixture is well kneaded with water, granulated and dried to obtain a granule.

FORMULATION EXAMPLE 4

Twenty five parts of any one of the present compounds (1), (12), (13), (24), (25), (36), (37), (48), (49) and (60), 3 parts of polyoxyethylene sorbitan monooleate, 3 parts of CMC and 69 parts of water are mixed and wet-pulverized until the particle size decreases to 5 microns or less. Thus, a suspension formulation is obtained.

That the present compounds are useful as an active ingredient for herbicides is shown by the following test examples. In the examples, the present compound (1) is shown by Compound No. in Table 1, and compounds used for comparison are shown by Compound symbol in Table 3.

TABLE 3

| Compound symbol | Structural formula | Remarks |
|---|---|---|
| A | [structure with OC₂H₅, OCH₃, CH₃, OCH₃ groups] | EP-0 249 708-A1 ($n_D^{23}$ 1.5271) |
| B | [structure with N(CH₃)₂, OCH₃, OCH₃ groups] | Comparative Compound ($n_D^{23}$ 1.5475) |
| C | [structure with OH, OCH₃, CH₃, OCH₃ groups] | EP-0 249 708-A1 |
| D | [structure with OCH₃, CH₃, OCH₃ groups] | EP-0 223 406-A1 (Compound No. 16) |
| E | [structure with CH₃, N—CH₃, OCH₃, OCH₃ groups] | Comparative Compound ($n_D^{19}$ 1.5298) |

The determination of the herbicidal activity and phytotoxicity was carried out as follows: When the states of emergence and growth of treated test plants (weeds and crops) at the time of determination were completely the same as or hardly different from those of untreated test plants, the value of determination was taken as "0". When the treated test plants were completely killed, or their emergence and growth were completely inhibited, the value of determination was taken as "5", and an interval between "0" and "5" was divided into four stages, i.e. "1", "2", "3" and "4". The evaluation was thus made in six stages.

TEST EXAMPLE 1

Soil surface treatment test in upland field soil

Cylindrical plastic pots of 10 cm in diameter and 10 cm in depth were filled with upland field soil, and seeds of Japanese millet, oats and velvetleaf were sowed in the respective pots and covered with soil. The test compounds were formulated into emulsifiable concentrates according to Formulation Example 2, and the prescribed amount of each emulsifiable concentrate was diluted with water corresponding to 10 liters/are and uniformly applied onto the whole soil surface by means of an automatic sprayer. After application, the test plants were cultivated for 19 days in a greenhouse, and the herbicidal activity was examined. The results are shown in the table below.

| Test compound | Dosage rate of active ingredient (g/ha) | Herbicidal activity | | |
|---|---|---|---|---|
| | | Japanese millet | Oats | Velvetleaf |
| (1) | 125 | 5 | 4 | 4 |
| (12) | 125 | 4 | 3 | 4 |
| (13) | 125 | 4 | 3 | 4 |
| (25) | 125 | 4 | 4 | 4 |
| (37) | 125 | 5 | 4 | 4 |
| (48) | 125 | 4 | 4 | 4 |
| (49) | 125 | 5 | 4 | 4 |
| A | 125 | 2 | 1 | 0 |
| B | 125 | 0 | 0 | 0 |
| C | 125 | 2 | 1 | 0 |
| D | 125 | 1 | 2 | 0 |
| E | 125 | 2 | 2 | 2 |

TEST EXAMPLE 2

Soil surface treatment test in upland field soil

Cylindrical plastic pots of 10 cm in diameter and 10 cm in depth were filled with upland field soil, and seeds of Japanese millet, were sowed in the respective pots and covered with soil. The test compounds were formulated into emulsifiable concentrates according to Formulation Example 2, and the prescribed amount of each emulsifiable concentrate was diluted with water corresponding to 10 liters/are and uniformly applied onto the whole soil surface by means of an automatic sprayer. After application, the test plants were cultivated for 19 days in a greenhouse, and the herbicidal activity was examined. The results are shown in the table below.

| Test compound | Dosage rate of active ingredient (g/ha) | Herbicidal activity Japanese millet |
|---|---|---|
| (60) | 125 | 4 |
| A | 125 | 2 |
| B | 125 | 0 |
| C | 125 | 2 |
| D | 125 | 1 |
| E | 125 | 2 |

TEST EXAMPLE 3

Foliar treatment test in upland field soil

Cylindrical plastic pots of 10 cm in diameter and 10 cm in depth were filled with upland field soil, and seeds of Japanese millet, oats, radish, velvetleaf and tall morningglory were sowed in the respective pots and cultivated for 8 days in a greenhouse.

Thereafter, the test compounds were formulated into emulsifiable concentrates according to Formulation Example 2, and the prescribed amount of each emulsifiable concentrate was diluted with a spreading agent-containing water corresponding to 10 liters/are and uniformly applied from above onto the whole foliar portion of the test plants by means of an automatic sprayer. After application, the tests plants were cultivated for 19 days in a greenhouse, and the herbicidal activity was examined.

The results are shown in the table below.

| Test compound | Dosage rate of active ingredient (g/ha) | Herbicidal activity | | | | |
|---|---|---|---|---|---|---|
| | | Japanese millet | Oats | Radish | Velvet leaf | Tall morning-glory |
| (1) | 125 | 4 | 4 | 4 | 4 | 3 |
| | 31 | 4 | 4 | 4 | 3 | 3 |
| (13) | 125 | 3 | 3 | 5 | 5 | 4 |
| (25) | 125 | 5 | 5 | 3 | 4 | 4 |
| | 31 | 4 | 4 | 3 | 4 | 3 |
| (36) | 125 | 4 | 5 | 5 | 5 | 4 |
| | 31 | 3 | 4 | 5 | 4 | 4 |
| (48) | 125 | 4 | 5 | 5 | 5 | 4 |
| (49) | 125 | 5 | 4 | 5 | 5 | 5 |
| A | 125 | 2 | 1 | 0 | 0 | 1 |
| | 31 | 2 | 0 | 0 | 0 | 1 |
| B | 125 | 0 | 0 | 0 | 0 | 0 |
| | 31 | 0 | 0 | 0 | 0 | 0 |
| C | 125 | 2 | 1 | 1 | 0 | 1 |
| | 31 | 1 | 0 | 0 | 0 | 0 |
| D | 125 | 1 | 1 | 0 | 0 | 2 |
| | 31 | 1 | 1 | 0 | 0 | 0 |
| E | 125 | 3 | 3 | 2 | 2 | 2 |
| | 31 | 2 | 2 | 2 | 1 | 1 |

TEST EXAMPLE 4

Flooding treatment test in paddy field

Cylindrical plastic pots of 8 cm in diameter and 12 cm in depth were filled with paddy field soil, and seeds of barnyardgrass and bulrush were sowed 1 to 2 cm deep under the soil surface. After creating the state of paddy field by flooding, a tuber of arrowhead was buried 1 to 2 cm deep under the soil surface and cultivated in a greenhouse. After 6 days (at the initial stage of generation of every weed), the test compounds were formulated into emulsifiable concentrates according to Formulation Example 2, and the prescribed amount of each emulsifiable concentrate was diluted with 2.5 ml of water and applied onto the water surface. After application, the test plants were cultivated for 19 days in a greenhouse, and the herbicidal activity was examined. The results are shown in the table below.

| Test compound | Dosage rate of active ingredient (g/ha) | Herbicidal activity | | |
|---|---|---|---|---|
| | | Barnyard-grass | Bulrush | Arrow-head |
| (1) | 250 | 4 | 4 | — |
| | 63 | 3 | 4 | — |
| (12) | 250 | 5 | 5 | 4 |
| | 63 | 5 | 5 | 4 |
| (13) | 250 | 4 | 5 | 4 |
| | 63 | 3 | 4 | 4 |
| (25) | 250 | 5 | 5 | 4 |
| | 63 | 4 | 5 | 4 |
| (36) | 250 | 4 | 4 | 4 |
| (37) | 250 | 5 | 5 | 4 |
| (48) | 250 | 5 | 5 | 4 |
| (49) | 250 | 4 | 5 | 4 |
| A | 250 | 3 | 1 | 3 |
| | 63 | 3 | 1 | 3 |
| B | 250 | 3 | 0 | 0 |
| | 63 | 1 | 0 | 0 |
| C | 250 | 3 | 2 | 3 |
| | 63 | 2 | 0 | 3 |
| D | 250 | 3 | 1 | 3 |

-continued

| Test compound | Dosage rate of active ingredient (g/ha) | Herbicidal activity | | |
|---|---|---|---|---|
| | | Barnyard-grass | Bulrush | Arrow-head |
| | 63 | 3 | 0 | 3 |

TEST EXAMPLE 5

Flooding treatment test in paddy field

Cylindrical plastic pots of 8 cm in diameter and 12 cm in depth were filled with paddy field soil. After creating the state of paddy field by flooding, a tuber of arrowhead was buried 1 to 2 cm deep under the soil surface. Also rice seedings of 2-leaf stage were transplanted into the pots. The weeds and crops were cultivated in a greenhouse. After 6 days (at the initial stage of generation of every weed), the test compounds were formulated into emulsifiable concentrates according to Formulation Example 2, and the prescribed amount of each emulsifiable concentrate was diluted with 2.5 ml of water and applied onto the water surface. After application, the test plants were cultivated for 19 days in a greenhouse, and the herbicidal activity and pytotoxicity were examined. The results are shown in the table below.

| Test compound | Dosage rate of active ingredient (g/ha) | Phytotoxicity Rice | Herbicidal activity Arrowhead |
|---|---|---|---|
| (37) | 16 | 0 | 4 |
| (49) | 16 | 0 | 4 |
| B | 16 | 0 | 0 |
| C | 16 | 0 | 0 |
| D | 16 | 0 | 2 |

TEXT EXAMPLE 6

Soil treatment test in upland field soil

Vats of $33 \times 23$ $cm^2$ in area and 11 cm in depth were filled with upland field soil, and seeds of corn barnyardgrass, johnsongrass and giant foxtail were sowed in the respective vats and covered with soil in a thickness of 1 to 2 cm. The test compounds were formulated into emulsifiable concentrates according to Formulation Example 2, and the prescribed amount of each emulsifiable concentrate was diluted with water corresponding to 10 liters/are and uniformly applied onto the whole soil surface by means of an automatic sprayer. After application, the test plants were cultivated for 18 days in a greenhouse, and the herbicidal activity and phytotoxicity were examined. The results are shown in Table below.

| Test compound | Dosage rate of active ingredient (g/ha) | Phyto-toxicity Corn | Herbicidal activity | | |
|---|---|---|---|---|---|
| | | | Barn-yard-grass | Giant foxtail | Johnson grass |
| (25) | 500 | 0 | 5 | 4 | 4 |
| A | 500 | 0 | 2 | 1 | 3 |
| B | 500 | 0 | 0 | 0 | 0 |
| C | 500 | 0 | 3 | 3 | 3 |
| D | 500 | 0 | 1 | 1 | 0 |

TEST EXAMPLE 7

Soil treatment test in upland field soil

Vats of 33×23 cm² in area and 11 cm in depth were filled with upland field soil, and seeds of tall morningglory, cocklebur, velvetleaf, sicklepod, black nightshade, barnyardgrass, johnsongrass and giant foxtail were sowed in the respective vats and covered with soil in a thickness of 1 to 2 cm. The test compounds were formulated into emulsifiable concentrates according to Formulation Example 2, and the prescribed amount of each emulsifiable concentrate was diluted with water corresponding to 10 liters/are and uniformly applied onto the whole soil surface by means of an automatic sprayer. After application, the test plants were cultivated for 18 days in a greenhouse, and the herbicidal activity was examined. The results are shown in Table below.

| Test compound | Dosage rate of active ingredient (g/ha) | Tall morning-glory | Cock-lebur | Velvet-leaf | Sick-lepod | Black night-shade | Barn-yard-grass | Giant foxtail | Johnson-grass |
|---|---|---|---|---|---|---|---|---|---|
| (49) | 63 | 4 | 4 | 4 | 4 | 4 | 4 | 4 | 4 |
| E | 125 | 0 | 0 | 0 | 2 | 1 | 1 | 1 | 3 |

TEST EXAMPLE 8

Soil treatment test in upland field soil

Vats of 33×23 cm² in area and 11 cm in depth were filled with upland field soil, and seeds of soybean, cotton, corn and velvetleaf were sowed in the respective vats and covered with soil in a thickness of 1 to 2 cm. The test compounds were formulated into emulsifiable concentrates according to Formulation Example 2, and the prescribed amount of each emulsifiable concentrate was diluted with water corresponding to 10 liters/are and uniformly applied onto the whole soil surface by means of an automatic sprayer. After application, the test plants were cultivated for 18 days in a greenhouse, and the herbicidal activity and phytotoxicity were examined. The results are shown in Table below.

| Test compound | Dosage rate of active ingredient (g/ha) | Phytotoxicity Soybean | Cotton | Corn | Herbicidal activity Velvetleaf |
|---|---|---|---|---|---|
| (37) | 500 | 1 | 0 | 0 | 5 |
|  | 125 | 0 | 0 | 0 | 4 |
| A | 500 | 2 | 2 | 0 | 0 |
| B | 500 | 0 | 0 | 0 | 0 |
| C | 500 | 0 | 0 | 0 | 0 |
| D | 500 | 0 | 0 | 0 | 0 |

Test Example 9

Foliar treatment test in upland field soil

Vats of 33×23 cm² in area and 11 cm in depth were filled with upland field soil, and seeds of velvetleaf, sicklepod, black nightshade, barnyardgrass, giant foxtail and johnsongrass were sowed in the respective vats and cultivated for 16 days. Thereafter, the test compounds were formulated into emulsifiable concentrates according to Formulation Example 2, and the prescribed amount of each emulsifiable concentrate was diluted with water corresponding to 10 liters/are and uniformly applied from above onto the whole foliar portion of the test plants by means of an automatic sprayer. The conditions of growth of the weeds at that time varied with the kind of the test plants, but the test plants were in the 0.5- to 2.5-leaf stage and were 5 to 15 cm in height. Eighteen days after application, the herbicidal activity and phytotoxicity were examined. The results are shown in Table below. This test was carried out in a greenhouse through the whole test period.

| Test compound | Dosage rate of active ingredient (g/ha) | Vel-vet-leaf | Sick-lepod | Black night-shade | Barn-yard-grass | Giant fox-tail | John-son-grass |
|---|---|---|---|---|---|---|---|
| (1) | 500 | 4 | 4 | 5 | 4 | 4 | 4 |
| (12) | 250 | 4 | 4 | 5 | 4 | 4 | 4 |
| (13) | 250 | 4 | 3 | 5 | 4 | 4 | 4 |
| (25) | 250 | 5 | 4 | 5 | 4 | 4 | 4 |
| (37) | 250 | 5 | 4 | 5 | 5 | 5 | 4 |
| A | 500 | 0 | 1 | 3 | 2 | 0 | 2 |
| B | 500 | 0 | 0 | 0 | 0 | 0 | 0 |
| C | 500 | 3 | 2 | 3 | 2 | 1 | 2 |

TEST EXAMPLE 10

Foliar treatment test in upland field soil

Vats of 33×23 cm² in area and 11 cm in depth were filled with upland field soil, and seeds of cron, tall morningglory, cocklebur, velvetleaf, sicklepod, barnyardgrass, giant foxtail and johnsongrass were sowed in the respective vats and cultivated for 16 days. Thereafter, the test compounds were formulated into emulsifiable concentrates according to Formulation Example 2, and the prescribed amount of each emulsifiable concentrate was diluted with water corresponding to 10 liters/are and uniformly applied from above onto the whole foliar portion of the test plants by means of an automatic sprayer. The conditions of growth of the weeds and crop at that time varied with the kind of the test plants, but the test plants were in the 0.5- to 4-leaf stage and were 5 to 30 cm in height. Eighteen days after application, the herbicidal activity and phytotoxicity were examined. The results are shown in Table below. This test was carried out in a greenhouse through the whole test period.

| Test compound | Dosage rate of active ingredient (g/ha) | Phyto-toxicity Corn | Tall morning-glory | Cock-lebur | Velvet-leaf | Sick-lepod | Barn-yard-grass | Giant foxtail | Johnson-grass |
|---|---|---|---|---|---|---|---|---|---|
| (36) | 250 | 0 | 4 | 5 | 5 | 5 | 5 | 5 | 5 |

-continued

| Test compound | Dosage rate of active ingredient (g/ha) | Phytotoxicity Corn | Herbicidal activity | | | | | | |
|---|---|---|---|---|---|---|---|---|---|
| | | | Tall morning-glory | Cocklebur | Velvetleaf | Sicklepod | Barnyardgrass | Giant foxtail | Johnsongrass |
| (48) | 63 | 0 | 4 | 3 | 5 | 4 | 4 | 4 | 4 |
| A | 500 | 1 | 1 | 0 | 0 | 1 | 2 | 0 | 2 |
| C | 500 | 0 | 1 | 0 | 3 | 2 | 2 | 1 | 2 |

TEST EXAMPLE 11

Foliar treatment test in upland field soil

Vats of 33×23 cm² in area and 11 cm in depth were filled with upland field soil, and seeds of cotton, velvetleaf, sicklepod, black nightshade, barnyardgrass, giant foxtail and johnsongrass were sowed in the respective vats and cultivated for 16 days. Thereafter, the test compounds were formulated into emulsifiable concentrates according to Formulation Example 2, and the prescribed amount of each emulsifiable concentrate was diluted with water corresponding to 10 liters/are and uniformly applied from above onto the whole foliar portion of the test plants by means of an automatic sprayer. The conditions of growth of the weeds and crop at that time varied with the kind of the test plants, but the test plants were in the 0.5- to 2.5-leaf stage and were 5 to 15 cm in height. Eighteen days after application, the herbicidal activity and phytotoxicity were examined. The results are shown in Table below. This test was carried out in a greenhouse through the whole test period.

| Test compound | Dosage rate of active ingredient (g/ha) | Phytotoxicity Cotton | Herbicidal activity | | | | | |
|---|---|---|---|---|---|---|---|---|
| | | | Velvetleaf | Sicklepod | Black nightshade | Barnyardgrass | Giant foxtail | Johnsongrass |
| (49) | 8 | 0 | 4 | 4 | 5 | 4 | 4 | 4 |
| E | 8 | 2 | 2 | 2 | 2 | 1 | 0 | 1 |

TEST EXAMPLE 12

Soil treatment test in upland field soil

Vats of 33×23 cm² in area and 11 cm in depth were filled with upland field soil, and seeds of beet, birdseye speedwell, field pansy, wild oat and blackgrass were sowed in the respective vats and covered with soil in a thickness of 1 to 2 cm. The test compounds were formulated into emulsifiable concentrates according to Formulation Example 2, and the prescribed amount of each emulsifiable concentrate was diluted with water corresponding to 10 liters/are and uniformly applied onto the whole soil surface by means of an automatic sprayer. After application, the test plants were cultivated for 25 days in a greenhouse, and the herbicidal activity and phytotoxicity were examined. The results are shown in Table below.

| Test compound | Dosage rate of active ingredient (g/ha) | Phytotoxicity Beet | Herbicidal activity | | | |
|---|---|---|---|---|---|---|
| | | | Birdseye speedwell | Field pansy | Wild oat | Blackgrass |
| (37) | 125 | 0 | 4 | 4 | 4 | 4 |
| A | 250 | 2 | 1 | 0 | 1 | 3 |
| B | 250 | 0 | 0 | 0 | 0 | 0 |
| C | 250 | 3 | 3 | 1 | 3 | 3 |
| D | 250 | 2 | 2 | 0 | 2 | 2 |
| E | 250 | 0 | 3 | 2 | 0 | 0 |

TEST EXAMPLE 13

Soil treatment test in upland field soil

Vats of 33×23 cm² in area and 11 cm in depth were filled with upland field soil, and seeds of pale smartweed, chickweed, birdseye speedwell, field pansy, downy brome, wild oat, blackgrass and annual bluegrass were sowed in the respective vats and covered with soil in a thickness of 1 to 2 cm. The test compounds were formulated into emulsifiable concentrates according to Formulation Example 2, and the prescribed amount of each emulsifiable concentrate was diluted with water corresponding to 10 liters/are and uniformly applied onto the whole soil surface by means of an automatic sprayer. After application, the test plants were cultivated for 25 days in a greenhouse, and the herbicidal activity was examined. The results are shown in Table below.

| Test compound | Dosage rate of active ingredient (g/ha) | Herbicidal activity | | | | | | | |
|---|---|---|---|---|---|---|---|---|---|
| | | Pale smartweed | Chickweed | Birdseye speedwell | Field pansy | Downy brome | Wild oat | Blackgrass | Annual bluegrass |
| (49) | 250 | 5 | 5 | 5 | 5 | 5 | 4 | 5 | 5 |
| A | 250 | 1 | 0 | 1 | 0 | 0 | 1 | 3 | 3 |
| B | 250 | 0 | 0 | 0 | 0 | 0 | 0 | 0 | 0 |
| C | 250 | 3 | 3 | 3 | 1 | 0 | 3 | 3 | 3 |
| D | 250 | 0 | 0 | 2 | 0 | 0 | 2 | 2 | 3 |
| E | 250 | 1 | 0 | 3 | 2 | 0 | 0 | 0 | 0 |

TEST EXAMPLE 14

Soil treatment test in upland field soil

Vats of 33×23 cm² in area and 11 cm in depth were filled with upland field soil, and seeds of wheat, barley, birdseye speedwell and field pansy were sowed in the respective vats and covered with soil in a thickness of 1 to 2 cm. The test compounds were formulated into emulsifiable concentrates according to Formulation Example 2, and the prescribed amount of each emulsifiable concentrate was diluted with water corresponding to 10 liters/are and uniformly applied onto the whole soil surface by means of an automatic sprayer. After application, the test plants were cultivated for 25 days in a greenhouse, and the herbicidal activity and phytotoxicity were examined. The results are shown in Table below.

| Test compound | Dosage rate of active ingredient (g/ha) | Phytotoxicity Wheat | Phytotoxicity Barley | Herbicidal activity Birdseye speedwell | Herbicidal activity Field pansy |
|---|---|---|---|---|---|
| (1) | 63 | 0 | 0 | 5 | 4 |
| (12) | 125 | 0 | 0 | 3 | 4 |
| A | 250 | 2 | 3 | 1 | 0 |
| C | 250 | 3 | 3 | 3 | 1 |
| D | 250 | 0 | 2 | 2 | 0 |
| E | 250 | 0 | 0 | 3 | 2 |

TEST EXAMPLE 15

Foliar treatment test in upland field soil

Vats of 33×23 cm² in area and 11 cm in depth were filled with upland field soil, and seeds of pale smartweed, chickweed, downy brome, wild oat and blackgrass were sowed in the respective vats and cultivated for 31 days. Thereafter, the test compounds were formulated into emulsifiable concentrates according to Formulation Example 2, and the prescribed amount of each emulsifiable concentrate was diluted with water corresponding to 10 liters/are and uniformly applied from above onto the whole foliar portion of the test plants by means of an automatic sprayer. The conditions of growth of the weeds at that time varied with the kind of the test plants, but the test plants were in the 1.5- to 5-leaf stage and were 5 to 25 cm in height. Twenty-five days after application, the herbicidal activity was examined. The results are shown in Table below. This test was carried out in a greenhouse through the whole test period.

| Test compound | Dosage rate of active ingredient (g/ha) | Pale smartweed | Chickweed | Downy brome | Wild oat | Blackgrass |
|---|---|---|---|---|---|---|
| (36) | 250 | 5 | 5 | 5 | 5 | 5 |
| (49) | 125 | 5 | 5 | 3 | 4 | 4 |
| A | 250 | 2 | 0 | 3 | 3 | 2 |
| B | 250 | 0 | 0 | 0 | 0 | 0 |
| D | 250 | 0 | 0 | 0 | 0 | 0 |
| E | 250 | 2 | 2 | 3 | 3 | 3 |

What is claimed is:

1. A pyrimidine derivative having the formula,

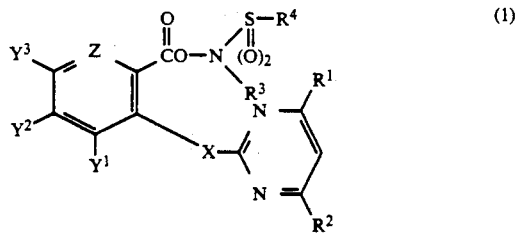

wherein each of $R^1$ and $R^2$, which may be the same or different, is $C_1-C_6$ alkyl, $C_1-C_6$ alkoxy, halo $C_1-C_6$ alkoxy or halogen;

$R^3$ is hydrogen or $C_1-C_6$ alkyl;

$R^4$ is $C_1-C_6$ alkyl, halo $C_1-C_6$ alkyl, benzyl, phenyl or phenyl substituted with at least one member selected from the group consisting of $C_1-C_6$ alkyl, $C_1-C_6$ alkoxy, halo $C_1-C_6$ alkyl, $C_1-C_6$ alkoxycarbonyl, nitro and halogen;

X is oxygen or sulfur;

Z is nitrogen or $CY^4$;

each of $Y^1$, $Y^2$ and $Y^3$, which may be the same or different, is hydrogen, halogen, $C_1-C_6$ alkyl or $C_1-C_6$ alkoxy; and $Y^4$ is hydrogen, hydroxyl, mercapto, nitro, halogen, $C_1-C_6$ alkyl, $C_2-C_6$ alkenyl, $C_2-C_6$ alkynyl, $C_1-C_6$ alkoxy, $C_3-C_6$ alkenyloxy, $C_3-C_6$ alkynyloxy, halo $C_1-C_6$ alkyl, halo $C_2-C_6$ alkenyl, halo $C_2-C_6$ alkynyl, halo $C_1-C_6$ alkoxy, halo $C_3-C_6$ alkenyloxy, halo $C_3-C_6$ alkynyloxy, $C_1-C_6$ alkoxy $C_1-C_6$ alkyl, $C_3-C_6$ alkenyloxy $C_1-C_6$ alkyl, $C_3-C_6$ alkynyloxy $C_1-C_6$ alkyl, cyano, formyl, carboxyl, $C_1-C_6$ alkoxycarbonyl, $C_3-C_6$ alkenyloxycarbonyl, $C_3-C_6$ alkynyloxycarbonyl, phenyl, phenyl substituted with at least one member selected from the group consisting of $C_1-C_6$ alkyl, $C_1-C_6$ alkoxy, halo $C_1-C_6$ alkyl, $C_1-C_6$ alkoxycarbonyl and halogen, phenoxy, phenoxy substituted with at least one member selected from the group consisting of $C_1-C_6$ alkyl, $C_1-C_6$ alkoxy, halo $C_1-C_6$ alkyl, $C_1-C_6$ alkoxycarbonyl and halogen, phenylthio, phenylthio substituted with at least one member selected from the group consisting of $C_1-C_6$ alkyl, $C_1-C_6$ alkoxy, halo $C_1-C_6$ alkyl, $C_1-C_6$ alkoxycarbonyl and halogen, benzyloxy, benzyloxy substituted with at least one member selected from the group consisting of $C_1-C_6$ alkyl, $C_1-C_6$ alkoxy, halo $C_1-C_6$ alkyl, $C_1-C_6$ alkoxycarbonyl and halogen, benzylthio, benzylthio substituted with at least one member selected from the group consisting of $C_1-C_6$ alkyl, $C_1-C_6$ alkoxy, halo $C_1-C_6$ alkyl, $C_1-C_6$ alkoxycarbonyl and halogen,

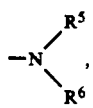

wherein each of $R^5$ and $R^6$, which may be the same or different is hydrogen, $C_1-C_6$ alkyl, $C_3-C_6$ alkenyl or $C_3-C_6$ alkynyl,

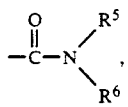

wherein $R^5$ and $R^6$ are as defined above,

wherein $R^7$ is $C_1$-$C_6$ alkyl, $C_3$-$C_6$ alkenyl or $C_3$-$C_6$ alkynyl and m is an integer of 0, 1 or 2,

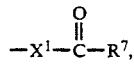

wherein $X^1$ is oxygen or sulfur, and $R^7$ is as defined above, or

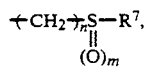

wherein $R^7$ and m are as defined above, and n is an integer of from 1 to 4.

2. A pyrimidine derivative according to claim 1, wherein each of $R^1$ and $R^2$, which may be the same or different, is $C_1$-$C_6$ alkoxy.

3. A pyrimidine derivative according to claim 1, wherein both $R^1$ and $R^2$ are methoxy.

4. A pyrimidine derivative according to claim 1, wherein Z is nitrogen or $CY^5$ wherein $Y^5$ is hydrogen, halogen, halo $C_1$-$C_6$ alkyl, $C_1$-$C_6$ alkyl, $C_1$-$C_6$ alkoxy, phenyl or phenyl substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl and halogen.

5. A pyrimidine derivative according to claim 1, wherein Z is nitrogen, CH, CF, CCl, CBr or CI.

6. A pyrimidine derivative according to claim 2, wherein Z is CF, CCl, CBr or CI.

7. A pyrimidine derivative according to claim 1, wherein both $Y^1$ and $Y^2$ are hydrogen or fluorine, and $Y^3$ is hydrogen, fluorine or $C_1$-$C_6$ alkoxy.

8. A pyrimidine derivative according to claim 1, wherein it has the formula,

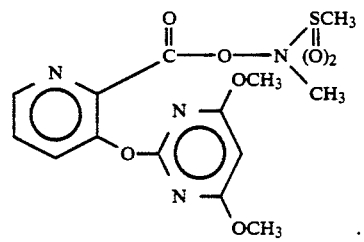

9. A pyrimidine derivative according to claim 1, wherein it has the formula,

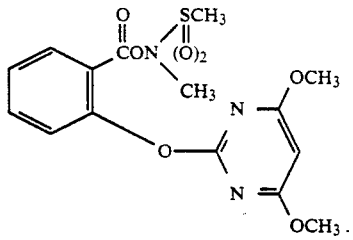

10. A pyrimidine derivative according to claim 1, wherein it has the formula,

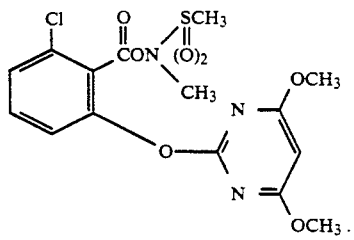

11. A compound having the formula,

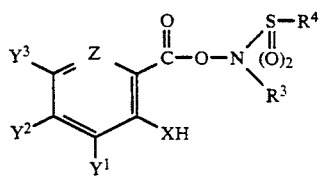

(2)

wherein $R^3$ is hydrogen or $C_1$-$C_6$ alkyl;

$R^4$ is $C_1$-$C_6$ alkyl, halo $C_1$-$C_6$ alkyl, benzyl, phenyl or phenyl substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl, nitro and halogen;

X is oxygen or sulfur;

Z is nitrogen or $CY^4$;

each of $Y^1$, $Y^2$ and $Y^3$, which may be the same or different, is hydrogen, halogen, $C_1$-$C_6$ alkyl or $C_1$-$C_6$ alkoxy; and $Y^4$ is hydrogen, hydroxyl, mercapto, nitro, halogen, $C_1$-$C_6$ alkyl, $C_2$-$C_6$ alkenyl, $C_2$-$C_6$ alkynyl, $C_1$-$C_6$ alkoxy, $C_3$-$C_6$ alkenyloxy, $C_3$-$C_6$ alkynyloxy, halo $C_1$-$C_6$ alkyl, halo $C_2$-$C_6$ alkenyl, halo $C_2$-$C_6$ alkynyl, halo $C_1$-$C_6$ alkoxy, halo $C_3$-$C_6$ alkenyloxy, halo $C_3$-$C_6$ alkynyloxy, $C_1$-$C_6$ alkoxy $C_1$-$C_6$ alkyl, $C_3$-$C_6$ alkenyloxy $C_1$-$C_6$ alkyl, $C_3$-$C_6$ alkynyloxy $C_1$-$C_6$ alkyl, cyano, formyl, carboxyl, $C_1$-$C_6$ alkoxycarbonyl, $C_3$-$C_6$ alkenyloxycarbonyl, $C_3$-$C_6$ alkynyloxycarbonyl, phenyl, phenyl substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl and halogen, phenoxy, phenoxy substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl and halogen, phenylthio, phenylthio substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl and halogen, benzyloxy, benzyloxy substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl and halogen, benzylthio, benzylthio substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl and halogen,

wherein each of $R^5$ and $R^6$, which may be the same or different, is hydrogen, $C_1$-$C_6$ alkyl, $C_3$-$C_6$ alkenyl or $C_3$-$C_6$ alkynyl,

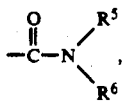

wherein $R^5$ and $R^6$ are as defined above,

wherein $R^7$ is $C_1$-$C_6$ alkyl, $C_3$-$C_6$ alkenyl or $C_3$-$C_6$ alkynyl and m is an integer of 0, 1 or 2,

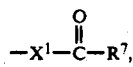

wherein $X^1$ is oxygen or sulfur, and $R^7$ is as defined above, or

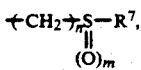

wherein $R^7$ and m are as defined above, and n is an integer of from 1 to 4.

12. A herbicidal composition which comprises as an active ingredient a herbicidally effective amount of a pyrimidine derivative having the formula,

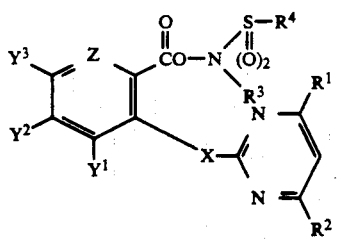 (1)

wherein each of $R^1$ and $R^2$, which may be the same or different, is $C_1$-$C_6$ alkyl, $C_1$-$C_6$ alkoxy, halo $C_1$-$C_6$ alkoxy or halogen;

$R^3$ is hydrogen or $C_1$-$C_6$ alkyl;

$R^4$ is $C_1$-$C_6$ alkyl, halo $C_1$-$C_6$ alkyl, benzyl, phenyl or phenyl substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl, nitro and halogen;

each of $Y^1$, $Y^2$ and $Y^3$, which may be the same or different, is hydrogen, halogen, $C_1$-$C_6$ alkyl or $C_1$-$C_6$ alkoxy; and $Y^4$ is hydrogen, hydroxyl, mercapto, nitro, halogen, $C_1$-$C_6$ alkyl, $C_2$-$C_6$ alkenyl, $C_2$-$C_6$ alkynyl, $C_1$-$C_6$ alkoxy, $C_3$-$C_6$ alkenyloxy, $C_3$-$C_6$ alkynyloxy, halo $C_1$-$C_6$ alkyl, halo $C_2$-$C_6$ alkenyl, halo $C_2$-$C_6$ alkynyl, halo $C_1$-$C_6$ alkoxy, halo $C_3$-$C_6$ alkenyloxy, halo $C_3$-$C_6$ alkynyloxy, $C_1$-$C_6$ alkoxy $C_1$-$C_6$ alkyl, $C_3$-$C_6$ alkenyloxy $C_1$-$C_6$ alkyl, $C_3$-$C_6$ alkynyloxy $C_1$-$C_6$ alkyl, cyano, formyl, carboxyl, $C_1$-$C_6$ alkoxycarbonyl, $C_3$-$C_6$ alkenyloxycarbonyl, $C_3$-$C_6$ alkynyloxycarbonyl, phenyl, phenyl substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl and halogen, phenoxy, phenoxy substituted with at least one member selected from the group consisting of $C_1$-$C_6$ alkyl, $C_1$-$C_6$ alkoxy, halo $C_1$-$C_6$ alkyl, $C_3$-$C_6$ alkoxycarbonyl and halogen, phenylthio, phenylthio substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl and halogen, benzyloxy, benzyloxy substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl and halogen, benzylthio, benzylthio substituted with at least one member selected from the group consisting of $C_1$-$C_6$ alkyl, $C_1$-$C_6$ alkoxy, halo $C_1$-$C_6$ alkyl, $C_1$-$C_a$ alkoxycarbonyl and halogen,

wherein each of $R^5$ and $R^6$, which may be the same or different, is hydrogen, $C_1$-$C_6$ alkyl, $C_3$-$C_6$ alkenyl or $C_3$-6 alkynyl,

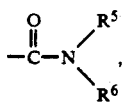

wherein $R^5$ and $R^6$ are as defined above,

wherein $R^7$ is $C_1$-$C_6$ alkyl, $C_3$-$C_6$ alkenyl or $C_3$-$C_6$ alkynyl and m is an integer of 0, 1 or 2,

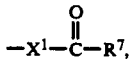

wherein $X^1$ is oxygen or sulfur, and $R^7$ is as defined above, or

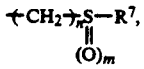

wherein $R^7$ and m are as defined above, and n is an integer of from 1 to 4; and an inert carrier or a diluent.

13. A method for controlling undesirable weeds, which comprises applying the herbicidal composition of claim 12 to an area where undesirable weeds grow or are likely to grow.

* * * * *